US012584082B2

(12) United States Patent
Fankhauser et al.

(10) Patent No.: US 12,584,082 B2
(45) Date of Patent: Mar. 24, 2026

(54) COMPOUNDS FOR A CONTROLLED RELEASE OF ACTIVE PERFUMING MOLECULES

(71) Applicant: FIRMENICH SA, Satigny (CH)

(72) Inventors: Peter Fankhauser, Satigny (CH); Andreas Herrmann, Satigny (CH); Umberto Maddalena, Satigny (CH); Alain Trachsel, Satigny (CH); Youqing Shen, Hangzhou (CN)

(73) Assignee: FIRMENICH SA, Satigny (CH)

( * ) Notice: Subject to any disclaimer, the term of this patent is extended or adjusted under 35 U.S.C. 154(b) by 366 days.

(21) Appl. No.: 17/462,482

(22) Filed: Aug. 31, 2021

(65) Prior Publication Data

US 2021/0395654 A1 Dec. 23, 2021

Related U.S. Application Data

(63) Continuation of application No. 14/386,809, filed as application No. PCT/EP2013/055641 on Mar. 19, 2013, now Pat. No. 11,155,772.

(30) Foreign Application Priority Data

Mar. 20, 2012 (EP) .................................... 12160253

(51) Int. Cl.

| | |
|---|---|
| ***C11D 3/50*** | (2006.01) |
| ***C07C 323/52*** | (2006.01) |
| ***C07C 323/60*** | (2006.01) |
| ***C07C 323/61*** | (2006.01) |
| ***C11B 9/00*** | (2006.01) |

(52) U.S. Cl.
CPC .............. *C11D 3/50* (2013.01); *C07C 323/52* (2013.01); *C07C 323/60* (2013.01); *C07C 323/61* (2013.01); *C11B 9/0011* (2013.01); *C11B 9/0034* (2013.01); *C11B 9/0042* (2013.01); *C11B 9/0057* (2013.01); *C11B 9/0061* (2013.01); *C11D 3/502* (2013.01); *C07B 2200/07* (2013.01); *C07C 2601/14* (2017.05); *C07C 2601/16* (2017.05); *C07C 2603/18* (2017.05); *C07C 2603/94* (2017.05)

(58) Field of Classification Search
CPC ......... C11D 3/50; C11D 3/502; C07C 323/52; C07C 323/60; C07C 323/61; C07C 2601/14; C07C 2601/16; C07C 2603/18; C07C 2603/94; C11B 9/0011; C11B 9/0034; C11B 9/0042; C11B 9/0057; C11B 9/0061; C07B 2200/07
See application file for complete search history.

(56) References Cited

U.S. PATENT DOCUMENTS

| | | | |
|---|---|---|---|
| 4,137,180 A | 1/1979 | Naik et al. | |
| 4,197,236 A | 4/1980 | Rosenberger et al. | |
| 5,236,615 A | 8/1993 | Trinh et al. | |
| 7,723,286 B2 * | 5/2010 | Fehr | C11D 3/507 510/106 |

(Continued)

FOREIGN PATENT DOCUMENTS

| | | |
|---|---|---|
| DE | 27 17 087 A1 | 11/1977 |
| EP | 0 799 885 A1 | 10/1997 |

(Continued)

OTHER PUBLICATIONS

International Search Report and Written Opinion, PCT/EP2013/055641, Jun. 25, 2013.

(Continued)

*Primary Examiner* — Angela C Brown-Pettigrew
*Assistant Examiner* — Preeti Kumar

(57) ABSTRACT

Described herein are compounds including at least one β-thio carbonyl or nitrile moiety capable of liberating an active molecule selected from an α,β-unsaturated ketone, aldehyde or nitrile. Also described herein are methods of using said compounds in perfumery as well as perfuming compositions or perfumed articles including the compounds. The compounds are represented by formula (I) where: a) m represents an integer from 1 to 6; b) Pro represents a hydrogen atom or a group susceptible of generating an odoriferous α,β-unsaturated ketone, aldehyde or nitrile and is represented by the formulae (II) or (II') in which the wavy line indicates the location of the bond between said Pro and the sulfur atom S; and at least one of the Pro groups is of the formula (II) or (II').

(I)

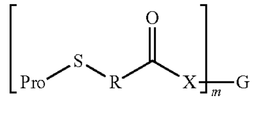

(II)

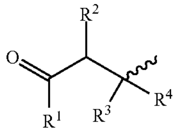

(II')

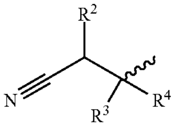

16 Claims, No Drawings

(56) References Cited

U.S. PATENT DOCUMENTS

| | | | | |
|---|---|---|---|---|
| 11,155,772 B2* | 10/2021 | Fankhauser | C11B 9/0057 | |
| 2008/0206158 A1* | 8/2008 | Miralles | A61K 8/046 514/576 | |
| 2011/0107524 A1* | 5/2011 | Chieffi | A23L 27/72 510/513 | |

FOREIGN PATENT DOCUMENTS

| | | | | |
|---|---|---|---|---|
| GB | 1 323 467 A | 7/1973 | | |
| WO | 97/34986 A1 | 9/1997 | | |
| WO | 03/049666 A2 | 6/2003 | | |
| WO | WO-2007007216 A2 * | 1/2007 | A61Q 13/00 | |
| WO | 2007/014409 A1 | 2/2007 | | |
| WO | 2008/044178 A1 | 4/2008 | | |
| WO | 2012/113746 A1 | 8/2012 | | |
| WO | WO-2016135193 A1 * | 9/2016 | A61K 8/447 | |

OTHER PUBLICATIONS

Aurich et al., "1,3-Dipolare Cycloaddition von Dinitronen—Bildung tricyclischer Dimerer / 1,3 -Dipolar Cycloaddition of Dinitrones—Formation of Tricyclic Dimers," Zeitschrift fur Naturforschung B, 49(7):963-969. (1994).

Berthier et al., "Influence of the Backbone Structure on the Release of Bioactive Volatiles from Maleic Acid-Based Polymer Conjugates, " Bioconjugate Chem., 21:2000-2012 (2010).

Esterbauer, "Kinetik der Reaktion von Sulfhydrylverbindungen mit α,β-ungesättigten Aldehyden in wäßrigem System," Monatshefte für Chemie, 101(3):782-810 (1970).

Fehr et al., "Aldols by Michael Addition: Application of the retro-Michael Addition to the Slow Release of Enones," Helvetica Chimica Acta, 88:3128-3136 (2005).

Hui et al., "Highly Enantioselective Conjugate Addition of Thioglycolate to Chalcones Catalyzed by Lanthanum: Low Catalyst Loading and Remarkable Chiral Amplification," Angew. Chem. Int. Ed., 49:4290-4293 (2010).

Hui et al., "Highly Enantioselective Conjugate Addition of Thioglycolate to Chalcones Catalyzed by Lanthanum: Low Catalyst Loading and Remarkable Chiral Amplification," Angew. Chem. Intl. Ed., 49(25):S1-S52 (2010).

Chata et al., "Synthesis and biological activity of enantiomeric pairs of 5-vinylthiolactomycin congeners," Bioorganic & Medicinal Chemistry Letters, 17(14):4070-4074 (2007).

Ranu et al., "Surface-Mediated Solid Phase Reaction : Dramatic Improvement of Michael Reaction on the Surface of Alumina," Tetrahedron, 48(7):1327-1332 (1992).

Birazieva et al., "New Thioterpenoids Based on Carvone," Chemistry of Natural Compounds, 42(6):693-695 (2006).

Vialemaringe et al., "Isomérisation de 2,3-époxypinanes fonctionnels en presence d'acides de Lewis," Helvetical Chimica Acta, 83:616-629 (2000).

* cited by examiner

COMPOUNDS FOR A CONTROLLED RELEASE OF ACTIVE PERFUMING MOLECULES

CROSS-REFERENCE TO RELATED APPLICATIONS

This application is a Continuation Application of application Ser. No. 14/386,809 filed Sep. 21, 2014, which is the U.S. national stage entry of PCT/EP2013/055641, filed on Mar. 19, 2013, which claims priority to European Patent Application 12160253, filed on Mar. 20, 2012, all of which are incorporated by reference in their entirety.

TECHNICAL FIELD

The present invention relates to the field of perfumery. More particularly, it concerns compounds comprising at least one β-thio carbonyl or nitrile moiety capable of liberating an active molecule such as, for example, an α,β-unsaturated ketone, aldehyde or nitrile. The present invention concerns also the use of said compounds in perfumery as well as the perfuming compositions or perfumed articles comprising the invention's compounds.

PRIOR ART

The perfume industry has a particular interest for compounds which are capable of prolonging the effect of active ingredients over a certain period of time, for example in order to overcome the problems encountered when using perfuming ingredients which are too volatile or have a poor substantivity. These compounds can be used in various applications, as for example in fine or functional perfumery. The washing of textiles is a particular field in which there is a constant quest to enable the effect of active substances, in particular perfumes, to be effective for a certain period of time after washing and drying. Indeed, many substances having fragrances which are particularly suitable for this type of application are, in fact, known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

Amongst the compounds of the present invention, only a few are known from the prior art. Said known compounds are phenylmethyl 2-[[1-methyl-1-(4-methyl-2-oxocyclohexyl)ethyl]thio]-acetate (mentioned in CAS but no reference reported), methyl 2-[[[(1S,2R,5R)-6,6-dimethyl-3-oxo-bicyclo[3.1.1]hept-2-yl]methyl]thio]-acetate (E. Mountaudon et al. in *Helv. Chim. Acta,* 2000, 83, 616), ethyl/methyl 2-((3-oxo-1,3-diphenylpropyl)thio)acetate and methyl 2-[(3-oxo-1-phenylbutyl)thio]-acetate (X. Feng et al. in *Angew. Chem. Int. Ed.,* 2010, 49, 4290), 2-((2-methyl-3-oxo-5-(prop-1-en-2-yl)cyclohexyl)thio)acetic acid and ethyl 2-((2-methyl-3-oxo-5-(prop-1-en-2-yl)cyclohexyl)thio)acetate (E. V. Sirazieva et al. in *Chem. Nat. Compd.,* 2006, 42, 693), 3-phenyl-2-propenenitrile (WO 03/029188). Other compounds similar to those of formula (I) have been described but they are not able to release a perfuming ingredient: 2-allyl-3-methyl-4-carboxymethylthio-2-cyclopentenone (U.S. Pat. No. 4,665,174), 14-O-[cyclohexanone-3(R/S)-yl)-sulfanylacetyl]-mutilin (WO 2007/014409), methyl 2-(((1-oxo-1,2,3,4-tetrahydronaphthalen-2-yl)(phenyl)methyl)thio)acetate and methyl 2-(((1-oxo-2,3-dihydro-1H-inden-2-yl)(phenyl)methyl)thio)acetate (supporting information of X. Feng et al. in *Angew. Chem. Int. Ed.,* 2010, 49, 4290).

However, all the compounds mentioned above have been used as synthetic intermediates and not as perfuming ingredients. Moreover, in the documents mentioned hereinabove, there is no mention or suggestion of the potential use of said compounds as perfuming ingredients and more specifically of the use of said compounds to control the release of active, e.g. odoriferous, molecules.

Some β-thio carbonyls are a known class of compound useful as perfumery ingredient (see WO 03/049666) which describe inter alia 3-(dodecylthio)-1-(2,6,6-trimethyl-3-cyclohexen-1-yl)-1-butanone. However, WO 03/049666 does not anticipate that the present compounds provided such increase performance.

DESCRIPTION OF THE INVENTION

We have, surprisingly, discovered the existence of compounds comprising at least one β-thio carbonyl or nitrile moiety and which are capable of liberating an active molecule. As "active molecule" we mean here any molecule capable of bringing an odor benefit or effect into its surrounding environment, and in particular an odoriferous molecule, i.e. a perfuming ingredient, such as an α,β-unsaturated ketone, aldehyde or nitrile. The invention's compounds are thus valuable perfuming ingredients.

Therefore a first aspect of the present invention concerns the compounds of formula

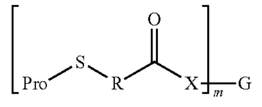

(I)

wherein:

a) m represents an integer from 1 to 6;

b) Pro represents a hydrogen atom or a group susceptible of generating an odoriferous α,β-unsaturated ketone, aldehyde or nitrile and is represented by the formulae

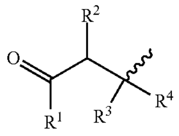

(II)

or

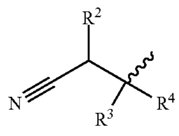

(II')

in which the wavy line indicates the location of the bond between said Pro and the sulfur atom S;

$R^1$ represents a hydrogen atom, a $C_1$ to $C_{15}$ linear, cyclic or branched alkyl, alkenyl or alkadienyl group, optionally substituted by $C_1$ to $C_4$ alkyl groups; and $R^2$, $R^3$ and $R^4$ represent a hydrogen atom, a $C_{6-9}$ aromatic group or a $C_1$ to $C_{15}$ linear, cyclic or branched alkyl, alkenyl or alkadienyl group, said $R^2$, $R^3$ and $R^4$ being optionally substituted by $C_1$ to $C_4$ alkyl groups; or two, or three, of the groups $R^1$ to $R^4$ are bonded together to form a saturated or unsaturated ring having 6 to 20 carbon atoms and including the carbon atom to which said $R^1$, $R^2$, $R^3$ or $R^4$ groups are bonded, this ring being optionally substituted by $C_{1-8}$ linear, branched or cyclic alkyl or alkenyl groups;

and with the proviso that at least one of the Pro groups is of the formula (II) or (II') as defined hereinabove;

c) X represents an oxygen atom or a $NR^5$ group, $R^5$ being a hydrogen atom or a $C_{1-10}$ hydrocarbon group;

d) R represents a divalent linear, branched or cyclic hydrocarbon group having from 1 to 6 carbon atoms optionally comprising a carboxylic acid or an alkaline carboxylate group; and e) G represents a hydrogen atom, an alkaline metal cation, an ammonium cation, or a multivalent $C_{1-22}$ hydrocarbon group (i.e. having a m valence) optionally comprising one silicium atom and/or from 1 or 2 functional groups selected from the group consisting of ether, alcohol, ester, ketone, quaternary amine or amine, or represents mono- or divalent $C_{4-30}$ hydrocarbon group comprising from 2 to 15 ether functional groups.

As "α,β-unsaturated ketone, aldehyde or nitrile", expression used in the definition of Pro, we mean here an α,β-unsaturated ketone, aldehyde or nitrile which is recognized by a person skilled in the art as being used in perfumery as perfuming ingredient. It is understood that said "odoriferous α,β-unsaturated ketone, aldehyde or nitrile" in order to be qualified as perfuming ingredient must be able to impart or modify in a positive or pleasant way the odor of a composition, and not just have an odor.

In general, said odoriferous α,β-unsaturated ketone, aldehyde or nitrile is a compound having from 8 to 20 carbon atoms, or even more preferably between 10 and 15 carbon atoms.

According to a particular embodiment of the invention, said group Pro represents a hydrogen atom or a group susceptible of generating an odoriferous α,β-unsaturated ketone, aldehyde or nitrile and is represented by the formulae (II)

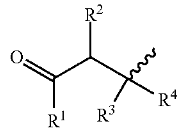

or (II')

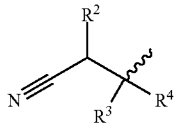

in which the wavy line indicates the location of the bond between said Pro and the sulfur atom S;

$R^1$ represents a hydrogen atom, a $C_1$ to $C_{10}$ linear, cyclic or branched alkyl, alkenyl or alkadienyl group, optionally substituted by one to four $C_{1-3}$ alkyl groups; and $R^2$ represents a hydrogen atom or a $C_{1-3}$ alkyl group or a phenyl group optionally substituted by one or two $C_{1-3}$ alkyl groups;

$R^3$ and $R^4$ represent a hydrogen atom, a phenyl group, a $C_{7-9}$ phenylalkyl group or a $C_1$ to $C_{10}$ linear, cyclic or branched alkyl, alkenyl or alkadienyl group, said $R^3$ and $R^4$ being optionally substituted by one to four $C_{1-4}$ alkyl groups;

or two, or three, of the groups $R^1$ to $R^4$ are bonded together to form a saturated or unsaturated ring having 6 to 12 carbon atoms and including the carbon atom to which said $R^1$, $R^2$, $R^3$ or $R^4$ groups are bonded, this ring being optionally substituted by one to four $C_{1-4}$ linear, branched or cyclic alkyl or alkenyl groups;

and with the proviso that at least one of the Pro groups is of the formula (II) or (II') as defined hereinabove.

According to a particular embodiment of the invention, said group Pro represents a hydrogen atom or a group of the formulae (P-1) to (P-16), in the form of any one of its isomers:

(P-1)

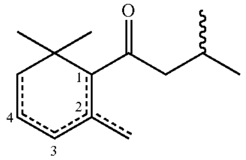

(P-2)

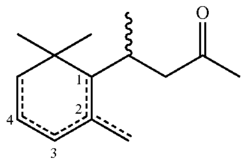

(P-3)

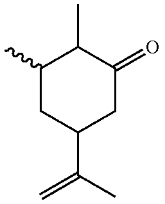

(P-4)

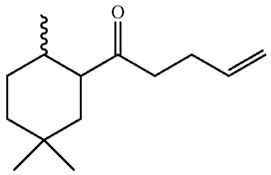

(P-5)

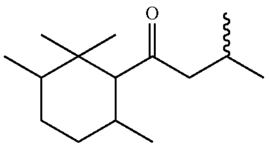

(P-6)

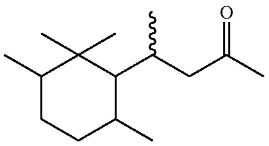

(P-7)

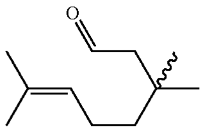

-continued (P-8)

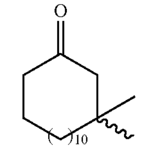

(P-9)

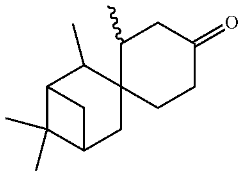

(P-10)

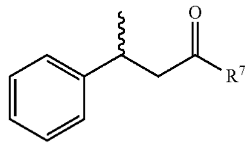

(P-11)

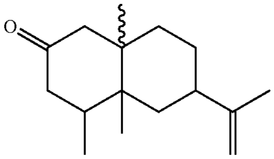

(P-12)

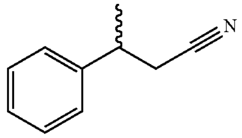

(P-13)

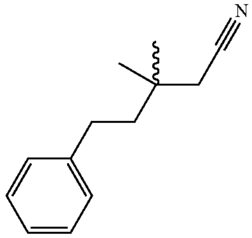

(P-14)

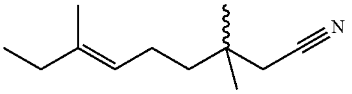

(P-15)

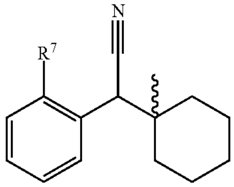

(P-16)

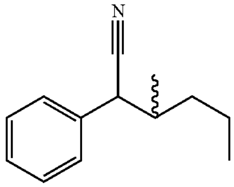

in which formulae the wavy line indicates the location of the bond between said Pro and the S atom, the dotted lines represent a single or double bond, $R^7$ indicating a hydrogen atom or a methyl group; and with the proviso that at least one of the Pro groups is of the formulae (P-1) to (P-16) as defined hereinabove.

According to any one of the invention's embodiments, said Pro group is a group susceptible of generating an odoriferous α,β-unsaturated ketone, aldehyde, or nitrile, and in particular an odoriferous α,β-unsaturated ketone or aldehyde.

According to any one of the invention's embodiments, said group Pro represents a hydrogen atom or a group susceptible of generating an odoriferous α,β-unsaturated ketone or aldehyde and is represented by the formula (II) as defined above.

According to any one of the invention's embodiments, said group Pro is a group of the formulae (P-1) to (P-11), as defined above.

According to any one of the invention's embodiments, said group Pro is a group of the formulae (P-1) to (P-7), as defined above.

According to any one of the invention's embodiments, said group Pro is a group susceptible of generating an odoriferous compound selected amongst: alpha-damascone, beta-damascone, gamma-damascone, delta-damascone, alpha-ionone, beta-ionone, gamma-ionone, delta-ionone, beta-damascenone, 3-methyl-5-propyl-2-cyclohexen-1-one, 1-(5,5- or 3,3-dimethyl-1-cyclohexen-1-yl)-4-penten-1-one, 2-methyl-5-(prop-1-en-2-yl)cyclohex-2-enone (carvone), 8- or 10-methyl-alpha-ionone, 2-octenal, 1-(2,2,3,6-tetramethyl-1-cyclohexyl)-2-buten-1-one, 4-(2,2,3,6-tetramethyl-1-cyclohexyl)-3-buten-2-one, 2-cyclopentadecen-1-one, nootkatone, cinnamic aldehyde, 2,6,6-trimethyl-bicyclo [3.1.1]heptane-3-spiro-2'-cyclohexen-4'-one and 3,7-dimethylocta-2,6-dienal (citral).

Amongst the odoriferous compounds cited in the list hereinabove, it will be preferably selected: the damascones, ionones, beta-damascenone, 1-(5,5- or 3,3-dimethyl-1-cyclohexen-1-yl)-4-penten-1-one, carvone, 1-(2,2,3,6-tetramethyl-1-cyclohexyl)-2-buten-1-one, 4-(2,2,3,6-tetramethyl-1-cyclohexyl)-3-buten-2-one and citral.

According to any one of the above embodiments of the invention, said group X is an oxygen atom or an $NR^5$ or NH group wherein $R^5$ is a $C_{1-6}$ alkyl group.

According to any one of the above embodiments of the invention, said group X is an oxygen atom or an NH group, in particular an oxygen atom.

According to any one of the above embodiments of the invention, said group R represents a linear or branched $C_1$-$C_3$, alkanediyl group optionally comprising a carboxylic acid or an alkaline carboxylate group. Specific, and non-limiting, examples of said R is a CH(Me), $CH_2$, $CH_2CH_2$, $CH_2CH_2CH_2$, $CH_2(CH_2)_2CH_2$, CH(Me)$CH_2$ or a CH($CH_2$COOH) or CH($CH_2$COOM) group, M being an alkaline metal cation.

According to any one of the above embodiments of the invention, said m is an integer from 1 to 4, in particular it represents 1 or 2. According to any one of the above embodiments of the invention, said m is 1.

According to any one of the above embodiments of the invention, said group G represents:

- a hydrogen atom, a sodium or potassium cation, an ammonium cation or a $C_{1-8}$ quaternary amine cation;
- a group of formula $Si(R^6)_{4-m}$, in which in is an integer from 1 to 4 and $R^6$ represents a $C_{1-8}$ hydrocarbon or alkoxyl group;
- a $C_{1-10}$, or even a $C_{1-7}$, linear, branched or cyclic alkyl, alkenyl or aromatic group optionally comprising from 1 or 2 ether, ester, quaternary amines or ketone functional groups (in which case m is 1);

a $C_{2-10}$ linear, branched or cyclic alkanediyl or benzenediyl group optionally comprising from 1 or 2 ether, ester, quaternary amines or ketone functional groups (in which case m is 2);

a $C_{4-10}$ branched or cyclic alkane-tri/tetra-yl group optionally comprising from 1 or 2 ether, ester, quaternary amines or ketone functional groups (in which case m is 3 or 4); or a $(CH_2CH_2O)_qR'$ group with R' being a hydrogen atom or a methyl group and with q being an integer varying between 3 and 12.

According to any one of the above embodiments of the invention, said group G represents:

a hydrogen atom, a sodium or potassium cation, the ammonium cation or a $C_{1-8}$ quaternary amine cation;

a group of formula $Si(R^6)_3$, $R^6$ represents a $C_{1-3}$ alkyl or alkoxyl group;

a $C_{1-5}$, or even a $C_{1-4}$, linear or branched alkyl group optionally comprising from 1 or 2 ether or quaternary amines functional groups; or a $(CH_2CH_2O)_qR'$ group with R' being a hydrogen atom or a methyl group and with q being an integer varying between 8 and 12.

According to any one of the above embodiments of the invention, said group G represents:

a hydrogen atom, a sodium or potassium cation, the ammonium cation or a $C_{1-8}$ quaternary amine cation; or a $C_{1-5}$, or even a $C_{1-4}$, linear or branched alkyl group.

According to any one of the above embodiments of the invention, said group G represents a hydrogen atom, a sodium or potassium cation, the ammonium cation or a $C_{1-8}$ quaternary amine cation, a $Si(Me)_3$ group or a methyl or ethyl group.

According to any one of the above embodiments of the invention, said moiety $G[X—CO—R—SH]_m$, in particular when in is 1, is a $C_{2-8}$ group, in particular a $C_{2-5}$ or a $C_{2-4}$ group.

Specific, and non-limiting, examples of said G group are the ones derived from the herein below examples of the $G[X—CO—R—SH]_m$ compounds, i.e. when it is mentioned 2-ethylhexyl 3-mercaptopropionate, the corresponding G group is a 2-ethylhexyl group and m is 1.

It is understood that by the expression "a linear, branched or cyclic . . . alkyl, alkenyl or aromatic group", or the similar, it is meant that said group can be in the form of, e.g., a linear alkyl group or can also be in the form of a mixture of said type of groups, e.g. a specific group may comprise a linear alkyl, a branched alkenyl, a (poly)cyclic alkyl and an aryl moiety, unless a specific limitation to only one type is mentioned. Similarly, in all the above and below embodiments of the invention, when a group is mentioned as being in the form of more than one type of topology (e.g. linear, cyclic or branched) and/or contains an unsaturation (e.g. alkyl, aromatic or alkenyl) it is meant also a group which may comprise moieties having any one of said topologies or unsaturations, as above explained. Similarly, in all the above and below embodiments of the invention when a group is mentioned as being in the form of a ring, said ring can be in a simple ring or a bicycle, a spiro cycle, and etc.

According to any one of the above embodiments, said compound (I) is a compound of formula (I')

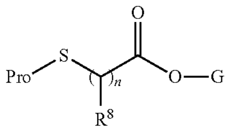

wherein Pro and G are as defined above, n is 1 or 2, and $R^8$ represents a hydrogen atom or a methyl group or a $CH_2COOH$ or a $CH_2COOM$ group, with M being defined as above.

When m in formula (I) is equal to 2, 3 or 4, then each of the various Pro may be identical or different, as well as each of the R.

The compounds of formula (I) may be synthesized from commercially available compounds by conventional methods. Generally speaking, the invention's compounds are obtainable by the [1,4]-addition reaction between an odoriferous α,β-unsaturated ketone, aldehyde or nitrile of formula (III)

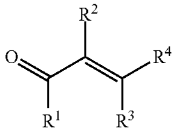

or (IV)

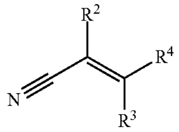

wherein the configuration of the carbon-carbon double bond can be of the E or Z type and the symbols $R^1$, $R^2$, $R^3$ and $R^4$ have the meaning indicated above; and a compound of formula $G[X—CO—R—SH]_m$, wherein all the symbols have the meaning given in formula (I).

A particular example of this approach is illustrated in the following scheme:

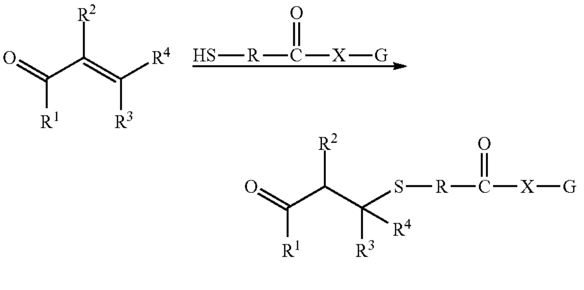

Specific examples or alternative approaches are described in the examples herein below.

Although it is not possible to provide an exhaustive list of the compounds of formula $G[X—CO—R—SH]_m$ which may be used in the synthesis of the invention's compounds, one can cite as preferred examples the following: thioglycolic acid, ammonium thioglycolate, 2-ethylhexyl thioglycolate, methyl thioglycolate, ethyl thioglycolate, 2,3-dihydroxypropyl 2-mercaptoacetate, (9H-fluoren-9-yl)methyl 2-mercapto acetate, trimethylolpropane tris(thioglycolate), pentaerythritol tetra(mercaptoacetate), 2-mercaptopropionic acid, ammonium 2-mercaptopropionate, methyl 2-mercaptopropionate, ethyl 2-mercaptopropionate, 2,3-dihydroxypropyl 2-mercaptopropionate, 1-hydroxyethyl 2-mercapto acetate, 2-hydroxypropyl 2-mercapto acetate, 3-hydroxypropyl 2-mercaptoacetate, 3-hydroxybutyl 2-mercaptoacetate, 4-hydroxybutyl 2-mercaptoacetate, 3-mercaptopropionic acid, methyl 3-mercaptopropionate, 3-mercapto-N,N-dimethylpropanamide, 2-ethylhexyl 3-mercaptopropionate, 3-methoxybutyl 3-mercaptopropionate, octadecyl 3-mercaptopropionate, butyl 3-mercaptopropionate, 3-mercapto-2-methylpropanoic acid, pentaerythritol tetra-(3-mercaptopropionate), trimethylolpropane tris-(3-mercaptopropionate), 2-mercaptosuccinic acid, 4-mercaptobutanoic acid, 2-hydroxyethyl 2-mercaptoacetate, 2-methoxyethyl 2-mercaptoacetate, 3-methoxybutyl thioglycolate, 2,5,8,11-tetraoxatridecan-13-yl 2-mercaptoacetate, 2,5,8,11,14,17,20,23,26,29,32,35-dodecaoxaheptatriacontan-37-yl 2-mercaptoacetate, ethane-1,2-diyl bis(2-mercaptoacetate), 1,4-butanediol bis(thioglycolate), and (ethane-1,2-diylbis(oxy))bis(ethane-2,1-diyl) bis(2-mercaptoacetate).

Particularly preferred compounds of formula G[X—CO—R—SH]$_m$ are the following: thioglycolic acid, ammonium thioglycolate, methyl thioglycolate, 2-mercaptopropionic acid, ammonium 2-mercaptopropionate, methyl 2-mercaptopropionate, 3-mercaptopropionic acid, methyl 3-mercaptopropionate, 3-mercapto-2-methylpropanoic acid and 2-mercaptosuccinic acid.

It is understood that the α,β-unsaturated ketone, aldehyde or nitrile of formulae (III) or (IV) are the odoriferous compounds released by the compound of formula (I) upon decomposition. An example of said decomposition reaction is illustrated in the following scheme:

(III)

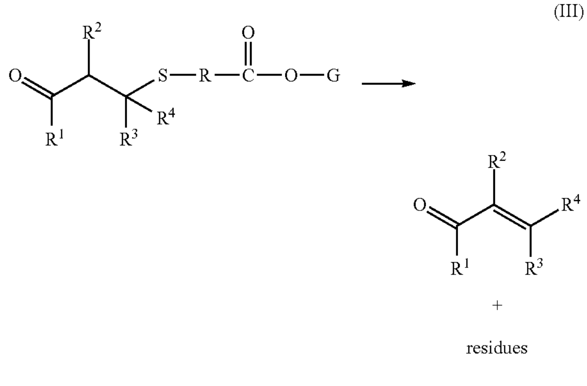

The residues of the decomposition reaction may be themselves odorless compounds, have themselves an odor or release a perfuming alcohol GOH. According to a particular embodiment, said residues are odorless compounds. Similarly, the compound of formula (I) is preferably odorless.

The decomposition reaction, which leads to the release of the odoriferous molecules, is believed to be influenced by pH changes, the presence of oxygen or other oxidants, enzymes or heat, but may be triggered by other types of mechanisms or the combination of several mechanisms.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also water (in which case a solubilizing amount of surfactants may be necessary), ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds, or can be an encapsulated perfume.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

Furthermore, the invention's compound can also be advantageously used in all the fields of modern perfumery, i.e. fine or functional perfumery, to positively impart or modify the odor of a consumer product into which said compound (I) is added. Indeed, for example, the invention's compounds are capable of levitating problems often encountered with classical perfuming ingredients present as such which in washing or perfuming compositions can have little staying-power on a surface and consequently are often eliminated, for example in the rinsing water or upon drying of surfaces such as textiles, hard surfaces, hair and skin.

Consequently, a perfuming consumer product which comprises:

i) as perfuming ingredient, at least one compound of formula (I), as defined above; and ii) a perfumery consumer base;

is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Preferred perfuming compositions or perfumed articles are perfumes, fabric or hard-surface detergents, hair care product or softener bases.

Typical examples of fabric detergents or softener compositions into which the compounds of the invention can be incorporated are described in WO 97/34986, in WO 2012/113756 or in U.S. Pat. Nos. 4,137,180 and 5,236,615 or in EP 799 885. Other typical detergents and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, New Jersey (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacement δ are indicated in ppm with respect to the TMS as standard, the coupling constants J are expressed in Hz.

Example 1

Synthesis of Compounds of Formula (I)

i) Synthesis of 2-((4-oxo-4-((1RS,2SR)-2,6,6-trimethylcyclohex-3-en-1-yl)butan-2-yl)thio)acetic acid (E)-1-((1RS,2SR)-2,6,6-trimethylcyclohex-3-enyl)but-2-en-1-one (delta-damascone; 47.0 g, 244 mmol) and 2-mercaptoacetic acid (22.0 g, 239 mmol) were stirred for 23 h at room temperature. The reaction mixture was diluted with methyl tert-butyl ether (MTBE; 35 ml), washed several times with $H_2O$ and concentrated under vacuum at a maximum temperature of 50° C. The crude title compound (60.0 g; ca. 1:1 diastereoisomeric mixture), containing some residual delta-damascone, can be used as such. A sample was further purified by flash chromatography on silica gel using a mixture of MTBE and n-heptane (10% up to 50% in MTBE) as the eluent.

$^{13}C$-NMR: 19.9 (q), 20.7 (q), 21.1/21.3 (q), 29.7 (q), 31.6/31.8 (d), 32.9/33.1 (t), 33.1/33.2 (s), 35.6 (d), 41.7 (t), 54.6/54.8 (t), 62.8/62.9 (d), 124.1/124.3 (d), 131.7/131.8 (d), 176.4/176.5 (s), 212.2/212.3 (s).

$^1H$-NMR: 0.87-0.92 (m, 3H); 0.94-1.01 (m, 6H); 1.32-1.37 (m, 3H); 1.66-1.74 (m, 1H); 1.92-2.01 (m, 1H); 2.19-2.25 (m, 1H); 2.46-2.62 (m, 1.5H); 2.75-2.79 (2s, 1H); 2.93-3.01 (m, 0.5H); 3.33-3.49 (m, 3H); 5.42-5.48 (m, 1H); 5.50-5.58 (m, 1H); 11.25 (s, 1H).

ii) Synthesis of 2-((3-oxo-1-(2,6,6-trimethylcyclohex-2-en-1-yl)pentyl)thio)acetic acid (E)-1-(2,6,6-trimethylcyclohex-2-enyl)pent-1-en-3-one (main isomer of an isomeric mixture; 10.0 g, 48.5 mmol) and ammonium thioglycolate (70% aqueous solution; 8.4 g, 53.9 mmol) were stirred at room temperature for 9 d. The reaction mixture was diluted with water (30 ml), then extracted with MTBE (30 ml) in order to remove unreacted substrate. The aqueous phase containing the ammonium carboxylates was acidified with aqueous HCl (10%) and extracted with MTBE (2×50 ml). The combined organic phases were washed with $H_2O$ and brine, dried over anhydrous $Na_2SO_4$, filtered and concentrated under vacuum (0.1 mbar) at a maximum temperature of 70° C. The crude target compound (5.1 g, viscous oil) can be used as such.

$^{13}C$-NMR: 7.7 (q), 22.8/23.1 (t), 25.2 (q), 27.5 (q), 28.5/28.7 (q), 31.1/31.7 (t), 33.4/33.5 (s), 34.6/35.5 (t), 36.6/36.7 (t), 40.0/41.9 (d), 47.6/50.1 (t), 54.2/55.1 (d), 123.7/124.9 (d), 132.0/133.3 (s), 176.1/176.6 (s), 210.1 (s).

$^1H$-NMR: 0.84-1.12 (m, 9H); 1.12-1.66 (m, 2H); 1.75-2.09 (m, 6H); 2.38-2.54 (m, 2H); 2.59-3.00 (m, 2H); 3.20-3.50 (m, 2H); 3.70-3.85 (m, 1H); 5.45-5.53 (m, 1H); 10.54 (s, 1H).

iii) Synthesis of 2-((2-formyl-1-phenyloctyl)thio)acetic acid

Using the same experimental procedure as described in Example ii, the title compound was obtained from hexylcinnamic aldehyde and ammonium thioglycolate. The crude title compound (28.9 g; pale yellow liquid; 2:1 diastereoisomeric mixture), containing some residual hexylcinnamic aldehyde, can be used as such. A sample was further purified by flash chromatography on silica gel using a mixture of MTBE and n-heptane (3% up to 80% in MTBE) as the eluent.

$^{13}C$-NMR: 14.0 (q), 22.4 (t), 26.5 (t), 28.5 (t), 28.9 (t), 31.4 (t), 31.7 (t), 49.3 (d), 56.3 (d), 128.1 (d), 128.7 (2d), 128.8 (2d), 138.3 (s), 175.4 (s), 202.1 (d).

$^1H$-NMR: 0.77-0.90 (m, 3H); 1.05-1.86 (m, 11H); 2.86-2.97 (m, 1H); 2.97-3.10 (m, 1H); 3.57-3.64 (m, 1H); 4.20-4.39 (m, 1H); 7.22-7.38 (m, 5H); 9.48-9.65 (m, 1H).

iv) Synthesis of ammonium 2-((4-oxo-4-((1RS,2SR)-2,6,6-trimethylcyclohex-3-en-1-yl)butan-2-yl)thio)acetate Delta-damascone (18.5 g, 96 mmol) and ammonium thioglycolate (70% aqueous solution; 16.5 g, 106 mmol) were stirred at room temperature for 42 h. The reaction mixture was diluted with water (50 ml), and then extracted with MTBE (2×30 ml). Remaining starting material (3.2 g) was recovered from the combined organic phases by removing the solvent under reduced pressure. The aqueous phase containing the target ammonium carboxylate was concentrated under vacuum yielding the target compound (28.0 g; ca. 1:1 diastereoisomeric mixture) as a white semi-crystalline material (97% yield).

$^{13}C$-NMR: 19.3/19.4 (q), 20.5 (q), 20.7/21.0 (q), 29.1 (q), 30.9/31.2 (d), 32.4/32.5 (s), 33.7 (d), 35.6/35.7 (t), 40.9 (t), 54.1 (t), 61.2/61.4 (d), 124.0/124.1 (d), 131.5 (d), 172.4 (s), 212.1/212.2 (s).

$^1H$-NMR: 0.81-0.87 (m, 6H); 0.92-0.97 (m, 3H); 1.16-1.22 (m, 3H); 1.61-1.70 (m, 1H); 1.91-2.01 (m, 1H); 2.24-2.41 (m, 2H); 2.49-2.54 (m, 1H); 2.70-2.78 (m, 1H); 3.04-3.09 (m, 2H); 3.20-3.29 (m, 1H); 5.41-5.47 (m, 1H); 5.50-5.56 (m, 1H); 6.80 (broad, $NH_4$).

v) Synthesis of trimethylsilyl 2-((4-oxo-4-((1RS,2SR)-2,6,6-trimethylcyclohex-3-en-1-yl)butan-2-yl)thio)acetate 2-((4-Oxo-4-((1RS,2SR)-2,6,6-trimethylcyclohex-3-en-1-yl)butan-2-yl)thio)acetic acid (Example i; 3.0 g, 10.6 mmol) and 2,2,2-trifluoro-N-methyl-N-(trimethylsilyl)acetamide (MSTFA; 3.0 ml) were heated at 40° C. for 4 h. The reaction mixture was purified by vacuum distillation (bulb to bulb distillation, 120° C., 0.1 mbar), affording 1.5 g of the title compound.

$^{13}C$-NMR: 0.33 (q), 19.9 (q), 20.7 (q), 21.2/21.4 (q), 29.8 (q), 31.6/31.8 (d), 33.1/33.2 (s), 34.7/34.8 (t), 35.3 (d), 41.7 (t), 54.8/54.9 (t), 62.8/62.9 (d), 124.1/124.3 (d), 131.7/131.8 (d), 170.8 (s), 212.0/212.1 (s).

$^1H$-NMR: 0.29-0.33 (m, 9H); 0.86-0.92 (m, 3H); 0.93-1.01 (m, 6H); 1.30-1.37 (m, 3H); 1.65-1.74 (m, 1H); 1.92-2.01 (m, 1H); 2.18-2.26 (m, 1H); 2.46-2.63 (m, 1.5H); 2.72-2.79 (m, 1H); 2.91-3.02 (m, 0.5H); 3.27-3.47 (m, 3H); 5.41-5.48 (m, 1H); 5.50-5.58 (m, 1H).

vi) Synthesis of methyl 2-((4-oxo-4-((1RS,2SR)-2,6,6-trimethylcyclohex-3-en-1-yl)butan-2-yl)thio)acetate Delta-damascone (36.0 g, 187 mmol) and methyl 2-mercaptoacetate (15.0 g, 141 mmol) were stirred for 15 d at room temperature, yielding a mixture of the target compound and delta-damascone. Removal of volatile impurities at 40° C. under high vacuum gave 47.5 g (93% weight yield) of a mixture which can be used as such. A pure sample (99%; two diastereoisomers ca. 1:1) was obtained by flash-chromatography (heptane/MTBE 95:5) on $SiO_2$.

$^{13}$C-NMR: 19.9 (q), 20.7 (q), 21.1/21.3 (q), 29.8 (q), 31.6/31.8 (d), 32.8/32.9 (t), 33.1/33.2 (s), 35.4 (d), 41.7 (t), 52.4 (t), 54.7/54.8 (t), 62.8/62.9 (d), 124.1/124.3 (d), 131.7/131.8 (d), 171.0 (s), 211.9/212.0 (s).

$^{1}$H-NMR: 0.87-0.92 (m, 3H); 0.94-1.01 (m, 6H); 1.32-1.37 (m, 3H); 1.66-1.74 (m, 1H); 1.93-2.01 (m, 1H); 2.19-2.25 (m, 1H); 2.46-2.60 (m, 2H); 2.73-2.77 (m, 1H); 3.29-3.47 (m, 3H); 3.739-3.743 (2s, 3H); 5.42-5.48 (m, 1H); 5.50-5.58 (m, 1H).

vii) Synthesis of methyl 2-((3-oxo-1-(2,6,6-trimethylcyclohex-2-en-1-yl)butyl)thio)acetate This compound was prepared by stirring (E)-4-(2,6,6-trimethylcyclohex-2-en-1-yl)but-3-en-2-one (alpha-ionone; 5.0 g, 26.0 mmol), 1,8-diazabicyclo[5.4.0]undec-7-ene (DBU; 0.25 g) and an excess of methyl 2-mercaptoacetate (10.0 g) at room temperature. After 11 h, the reaction was quenched with aqueous citric acid. The reaction mixture was diluted with MTBE (15 ml), washed several times with $H_2O$, then with brine, dried over anhydrous $Na_2SO_4$, filtered and concentrated under vacuum at a maximum temperature of 50° C. The crude title compound (16.0 g), containing some residual alpha-ionone, can be used as such. A sample was further purified by flash-chromatography (heptane/MTBE 70:30) on $SiO_2$.

$^{13}$C-NMR: 22.9/23.1 (t), 25.3/25.9 (q), 27.3/27.4 (q), 28.6/29.1 (q), 30.6 (q), 31.7 (t), 33.3/33.5 (s), 35.3 (t), 39.6 (d), 48.5/48.7 (t), 52.4/52.6 (q), 54.7/55.0 (d), 123.1/123.7 (d), 133.4/133.8 (s), 171.0/171.3 (s), 206.7 (s).

$^{1}$H-NMR: 0.87 (s, 0.7H); 0.92 (s, 2.3H); 1.02 (s, 3H); 1.10-1.33 (m, 2H); 1.46 (s, 1H); 1.78-1.88 (m, 3H); 1.94-2.05 (m, 3H); 2.15 (s, 2H); 2.67-2.75 (m, 1H); 3.25-3.39 (m, 2H); 3.73-3.82 (m, 5H); 5.40-5.50 (m, 1H).

viii) Synthesis of (E)-methyl 2-((1-cyano-2,6-dimethyloct-5-en-2-yl)thio)acetate-(Z)-methyl 2-((1-cyano-2,6-dimethyloct-5-en-2-yl)thio)acetate mixture Using the same experimental procedure as described in Example vii the title compound was obtained from 3,7-dimethylnona-2,6-dienenitrile (Lemonile®; origin: Givaudan SA) and methyl 2-mercaptoacetate. The crude target compound (isomeric mixture (Z/E) 40:60; still containing some residual Lemonile®) can be used as such. Purification by vacuum distillation (bulb to bulb distillation, 135-140° C., 0.1 mbar) afforded >99% pure title compound mixture.

$^{13}$C-NMR (deduced from the mixture): major isomer (E), 55% of the mixture, 12.7 (q), 16.0 (q), 22.9 (t), 25.5 (q), 30.6 (t), 30.9 (t), 32.3 (t), 39.6 (t), 46.9 (s), 52.7 (q), 116.9 (s), 121.2 (d), 138.3 (s), 170.9 (s); minor isomer (Z), 45% of the mixture, 12.8 (q), 16.0 (q), 22.6 (t), 24.8 (t), 25.5 (q), 30.6 (2t), 39.9 (t), 46.9 (s), 52.7 (q), 116.9 (s), 122.3 (d), 138.6 (s), 170.9 (s).

$^{1}$H-NMR: 0.95-1.01 (m, 3H); 1.43-1.46 (m, 3H); 1.61-1.63 (m, 2H); 1.66-1.74 (m, 3H); 1.94-2.19 (m, 4H); 2.69-2.73 (m, 2H); 3.28-3.32 (m, 2H); 3.75 (s, 3H); 5.01-5.12 (m, 1H).

ix) Synthesis of 2,3-dihydroxypropyl 2-((4-oxo-4-((1RS,2SR)-2,6,6-trimethylcyclohex-3-en-1-yl)butan-2-yl)thio)acetate This compound was prepared by stirring delta-damascone (15.0 g, 78 mmol)), DBU (0.3 g) and a slight excess glycerol monothioglycolate (17.5 g) at room temperature. After 2.5 h the reaction was quenched with aqueous citric acid. The reaction mixture was diluted with methylene chloride (15 ml), washed several times with $H_2O$ then brine, dried over anhydrous $Na_2SO_4$, filtered and concentrated under high vacuum at a maximum temperature of 50° C. The crude title compound (21.9 g; mixture of diastereoisomers; 78% yield) can be used as such.

$^{13}$C-NMR: 19.9 (q), 20.7 (q), 21.2/21.3 (q), 29.7/29.8 (q), 31.6/31.7 (d), 32.8/32.9 (t), 33.2 (s), 34.9/35.0 (d), 41.6/41.7 (t), 54.6/54.7 (t), 63.0 (d), 63.2/63.3 (t), 66.2/66.3 (t), 69.9/70.0 (d), 124.1/124.3 (d), 131.6/131.8 (d), 170.7 (s), 211.8/211.9 (s).

$^{1}$H-NMR: 0.85-1.04 (m, 9H); 1.28-1.37 (m, 3H); 1.65-1.75 (m, 1H); 1.83-2.13 (m, 2H); 2.19-2.25 (m, 1H); 2.46-2.62 (m, 1.5H); 2.73-2.77 (m, 1H); 2.89-2.98 (m, 0.5H); 3.26-3.54 (m, 4H); 3.60-3.69 (m, 1H); 3.70-4.048 (m, 2H); 4.16-4.33 (m, 2H); 5.42-5.48 (m, 1H); 5.50-5.58 (m, 1H).

x) Synthesis of 3-methoxybutyl 2-((4-oxo-4-((1RS,2SR)-2,6,6-trimethylcyclohex-3-en-1-yl)butan-2-yl)thio)acetate Delta-damascone (14.0 g, 72.8 mmol), DBU (0.25 g) and 3-methoxybutyl 2-mercaptoacetate (12.0 g, 67.3 mmol) were stirred at room temperature. After 3 h the reaction was quenched with aqueous citric acid. The reaction mixture was diluted with MTBE (10 ml), washed several times with $H_2O$, then with brine, dried over anhydrous $Na_2SO_4$, filtered and concentrated under high vacuum at a maximum temperature of 50° C. The crude title compound (24.1 g; mixture of diastereoisomers) can be used as such. Further purification by vacuum distillation (bulb to bulb distillation, 170-200° C., 0.1 mbar) afforded 15.0 g (60% yield) of pure title compound.

$^{13}$C-NMR: 19.1 (q), 19.9 (q), 20.7 (q), 21.1/21.3 (q), 29.8 (q), 31.6/31.8 (d), 33.0/33.1 (t), 33.1/33.2 (s), 35.3 (d), 35.5 (t), 41.7 (t), 54.7/54.8 (t), 56.1 (q), 62.4 (t), 62.8/62.9 (d), 73.5 (d), 124.1/124.3 (d), 131.7/131.8 (d), 170.5 (s), 211.8/211.9 (s).

$^{1}$H-NMR: 0.87-0.92 (m, 3H); 0.94-1.01 (m, 6H); 1.15-1.20 (m, 3H), 1.30-1.35 (m, 3H); 1.66-1.74 (m, 1H); 1.74-1.87 (m, 2H), 1.93-2.01 (m, 1H); 2.19-2.25 (m, 1H); 2.46-2.60 (m, 2H); 2.73-2.77 (m, 1H); 3.27-3.35 (m, 5H); 3.39-348. (m, 2H), 4.20-4.27 (m, 2H), 5.42-5.48 (m, 1H); 5.50-5.58 (m, 1H).

xi) Synthesis of 2-ethylhexyl 2-((4-oxo-4-((1RS,2SR)-2,6,6-trimethylcyclohex-3-en-1-yl)butan-2-yl)thio)acetate Delta-damascone (14.12 g, 73.4 mmol) and 2-ethylhexyl 2-mercaptoacetate (10.0 g, 48.9 mmol) were stirred at room temperature for 72 h. The resulting mixture, containing the title compound and some residual delta-damascone, can be used as such. A sample of the pure target compound was obtained by bulb to bulb distillation (180° C., 0.1 mbar).

$^{13}$C-NMR: 11.0 (q), 14.0 (q), 19.9 (q), 20.7 (q), 21.1/21.3 (q), 23.0 (t), 23.7 (t), 28.9 (t), 29.8 (q), 30.3 (t), 31.6/31.8 (d), 33.0/33.1 (t), 33.1/33.3 (s), 35.3 (d), 38.7 (d), 41.7 (t), 54.7/54.8 (t), 62.8/62.9 (d), 67.8 (t), 124.1/124.3 (d), 131.7/131.8 (d), 170.8 (s), 211.8/211.9 (s).

$^{1}$H-NMR: 0.87-0.92 (m, 9H); 0.94-1.01 (m, 6H); 1.26-1.42 (m, 11H); 1.55-1.74 (m, 2H); 1.92-2.01 (m, 1H); 2.18-2.24 (m, 1H); 2.52 (m, 1H); 2.56, 2.96 (m, 1H); 2.73-2.77 (2s, 1H); 3.27-3.32 (m, 2H); 3.38-3.48 (m, 1H); 4.01-4.10 (m, 2H); 5.41-5.48 (m, 1H); 5.50-5.58 (m, 1H).

xii) Synthesis of 2-ethylhexyl 2-((3-oxo-1-(2,6,6-trimethylcyclohex-2-en-1-yl)pentyl)thio)acetate This compound was prepared by stirring (E)-1-(2,6,6-trimethylcyclohex-2-enyl)pent-1-en-3-one (main isomer of an isomeric mixture; 10.0 g, 48.5 mmol), DBU (1.0 g) and 2-ethylhexyl 2-mercaptoacetate (15.0 g, 73.4 mmol) at room temperature. After 1 h the reaction was quenched with aqueous citric acid. The reaction mixture was diluted with MTBE (10 ml), washed with $H_2O$ and brine, dried over anhydrous $Na_2SO_4$, filtered and concentrated under high vacuum (0.1 mbar) at a maximum temperature of 140° C. The crude title compound (16.0 g; mixture of diastereoisomers, ratio 44:26:26:3 by NMR) can be used as such.

$^{13}$C-NMR (major isomer): 7.7 (q), 11.0 (q), 14.0 (q), 22.9 (t), 23.0 (t), 23.7 (t), 25.3 (q), 27.6 (q), 28.6 (q), 28.9 (t), 30.3 (t), 31.7 (t), 33.5 (s), 35.7 (t), 36.6 (t), 38.7 (d), 40.0 (d), 47.5 (t), 55.0 (d), 67.8 (t), 123.6 (d), 133.6 (s), 170.8 (s), 209.4 (s).

$^{1}$H-NMR (major isomer): 0.85-1.00 (m, 11H); 1.00-1.19 (m, 6H); 1.23-1.43 (m, 10H); 1.53-1.76 (m, 2H); 1.77-1.90 (m, 4H); 1.90-2.07 (m, 3H); 2.36-3.91 (m, 3H); 3.96-4.14 (m, 2H); 5.38-5.52 (m, 1H).

xiii) Synthesis of (9H-fluoren-9-yl)methyl 2-((4-oxo-4-((1RS,2SR)-2,6,6-trimethylcyclohex-3-en-1-yl)butan-2-yl)thio)acetate Methyl 2-(4-oxo-4-((1S,2R)-2,6,6-trimethylcyclohex-3-enyl)butan-2-ylthio)acetate (Example vi; 24.0 g, 52.3 mmol), dioctylstannanone (0.6 g), 9-fluorenylmethanol (10.0 g, 51.0 mmol) and n-heptane (50 ml) were refluxed for 4 h with azeotropic removal of methanol. The solvent as well as some of the remaining starting material was removed under high vacuum (0.1 mbar, 120° C.). Flash-chromatography (heptane/MTBE 95:5) on $SiO_2$ yielded the target compound (12.7 g, 53% yield).

$^{13}$C-NMR: 19.9 (q), 20.7 (q), 21.2/21.3 (q), 29.8 (q), 31.6/31.8 (d), 33.1 (s), 33.1/33.2 (t), 35.4 (d), 41.7 (t), 46.7 (d), 54.7/54.8 (t), 62.7/62.8 (d), 67.3 (t), 120.0 (d), 124.1/124.2 (d), 125.1 (d), 127.1 (d), 127.8 (d), 131.7/131.8 (d), 141.3 (s), 143.6 (s), 170.4 (s), 211.8/211.9 (s).

$^{1}$H-NMR: 0.85-0.90 (m, 3H); 0.91-0.98 (m, 6H); 1.28-1.34 (m, 3H); 1.63-1.72 (m, 1H); 1.90-1.99 (m, 1H); 2.16-2.22 (m, 1H); 2.46-2.59 (m, 1.5H); 2.73-2.77 (m, 1H); 2.91-2.99 (m, 0.5H); 3.34-3.47 (m, 3H); 4.20-4.27 (m, 1H); 4.41-4.44 (m, 2H); 5.40-5.47 (m, 1H); 5.50-5.57 (m, 1H); 7.28-7.35 (m, 2H); 7.36-7.43 (m, 2H); 7.62-7.77 (m, 2H); 7.74-7.78 (m, 2H).

xiv) Synthesis of 4-(2-mercaptoacetoxy)butyl 2-((4-oxo-4-((1RS,2SR)-2,6,6-trimethylcyclohex-3-en-1-yl)butan-2-yl)thio)acetate Delta-damascone (8.0 g, 41.6 mmol) and butane-1,4-diyl bis(2-mercaptoacetate) (8.0 g, 33.6 mmol) were stirred for 16 h at room temperature yielding a mixture of the target compound, delta-damascone and (S,R)-butane-1,4-diylbis(2-((4-oxo-4-((1RS,2SR)-2,6,6-trimethylcyclohex-3-en-1-yl)butan-2-yl)thio)acetate). This mixture (16.0 g) can be used as such. A pure sample (96%; two diastereoisomers ca. 1:1) was obtained by flash-chromatography (heptane/MTBE 60:40) on $SiO_2$.

$^{13}$C-NMR: 19.9 (q), 20.8 (q), 21.2/21.4 (q), 25.1 (t), 25.2 (t), 26.5 (t), 29.8 (q), 31.6/31.8 (d), 33.0/33.1 (t), 33.1/33.2 (s), 35.3 (d), 41.7 (t), 54.7/54.8 (t), 62.8/62.9 (d), 64.7 (t), 65.1 (t), 124.1/124.3 (d), 131.7/131.8 (d), 170.5/170.6 (s), 170.8 (s), 211.9/212.0 (s).

$^{1}$H-NMR: 0.87-0.92 (m, 3H); 0.93-1.01 (m, 6H); 1.30-1.35 (m, 3H); 1.72-1.79 (m, 5H); 1.92-2.04 (m, 2H); 2.18-2.24 (m, 1H); 2.45-2.59 (m, 1.5H); 2.72-2.76 (m, 1H); 2.91-2.99 (m, 0.5H); 3.23-3.32 (m, 4H); 3.39-3.47 (m, 1H); 4.14-4.21 (m, 4H); 5.42-5.48 (m, 1H); 5.50-5.58 (m, 1H).

xv) Synthesis of (S,R)-butane-1,4-diylbis(2-((4-oxo-4-((1RS,2SR)-2,6,6-trimethylcyclohex-3-en-1-yl)butan-2-yl)thio)acetate)

Using the same experimental procedure as described in Example xiv, but allowing a longer reaction time (66 h) gave a mixture (14 g) containing the title compound as the major ingredient. A pure sample (98%; two diastereoisomers ca. 1:1) was obtained by flash-chromatography (heptane/MTBE 70:30) on $SiO_2$.

$^{13}$C-NMR: 19.9 (q), 20.7 (q), 21.2/21.4 (q), 25.2 (t), 29.8 (q), 31.6/31.8 (d), 33.1/33.2 (s), 33.0/33.1 (t), 35.3 (d), 41.7 (t), 54.7/54.8 (t), 62.8/62.9 (d), 64.8 (t), 124.1/124.3 (d), 131.7/131.8 (d), 170.5 (s), 211.8/211.9 (s).

$^{1}$H-NMR: 0.87-0.92 (m, 6H); 0.93-1.01 (m, 12H); 1.30-1.35 (m, 6H); 1.66-1.78 (m, 6H); 1.92-2.01 (m, 2H); 2.18-2.24 (m, 2H); 2.46-2.59 (m, 3H); 2.73-2.77 (m, 2H); 2.91-2.99 (m, 1H); 3.27-3.33 (m, 4H); 3.39-3.47 (m, 2H); 4.14-4.21 (m, 4H); 5.42-5.48 (m, 2H); 5.50-5.58 (m, 2H).

xvi) Synthesis of (S,R)-2-ethyl-2-((2-((4-oxo-4-((1RS,2SR)-2,6,6-trimethylcyclohex-3-en-1-yl)butan-2-yl)thio)acetoxy)methyl)propane-1,3-diyl bis(2-((4-oxo-4-((1S,2R)-2,6,6-trimethylcyclohex-3-en-1-yl)butan-2-yl)thio)acetate)

Delta-damascone (33.0 g, 172 mmol) and 2-ethyl-2-((2-mercaptoacetoxy)methyl)propane-1,3-diyl bis(2-mercaptoacetate) (10.5 g, 29.5 mmol) were stirred for 12 d at room temperature yielding a mixture of delta-damascone, the target compound, (S,R)-2-ethyl-2-((2-mercaptoacetoxy)methyl)propane-1,3-diyl bis(2-((4-oxo-4-((1RS,2SR)-2,6,6-trimethylcyclohex-3-en-1-yl)butan-2-yl)thio)acetate) and 2-ethyl-2-((2-((4-oxo-4-((1RS,2SR)-2,6,6-trimethylcyclohex-3-en-1-yl)butan-2-yl)thio)acetoxy)methyl)propane-1,3-diyl bis(2-mercaptoacetate). Removal of traces of volatile impurities under high vacuum at 50° C. gave a mixture (42.0 g) that can be used as such. A pure sample (90%) of the title compound was obtained by flash-chromatography (heptane/MTBE 70:30) on $SiO_2$.

$^{13}$C-NMR: 7.38 (q), 19.9 (q), 20.7 (q), 21.2/21.4 (q), 29.8 (q), 31.6/31.8 (d), 32.9/33.0 (t), 33.1/33.2 (s), 35.4 (d), 41.1 (s), 41.7 (t), 54.7/54.8 (t), 62.8/62.9 (d), 64.5 (t), 124.1/124.3 (d), 131.7/131.8 (d), 170.1 (s), 211.7/211.8 (s).

$^{1}$H-NMR: 0.86-0.92 (m, 12H); 0.93-1.00 (m, 18H); 1.29-1.34 (m, 9H); 1.50-1.57 (m, 2H), 1.66-1.74 (m, 3H); 1.93-2.01 (m, 3H); 2.18-2.24 (m, 3H); 2.47-2.97 (m, 9H); 3.30-3.34 (m, 6H); 3.36-3.46 (m, 3H); 4.12 (s, 6H); 5.42-5.48 (m, 3H); 5.50-5.57 (m, 3H).

xvii) Synthesis of 2-((2-mercaptoacetoxy)methyl)-2-((2-((4-oxo-4-((1RS,2SR)-2,6,6-trimethylcyclohex-3-en-1-yl)butan-2-yl)thio)acetoxy)methyl)propane-1,3-diylbis(2-mercaptoacetate)

Delta-damascone (27.0 g, 140 mmol) and pentaerythritol tetrakis(2-mercaptoacetate) (10.0 g, 23.1 mmol) were stirred for 14 d at room temperature yielding a mixture of delta-damascone, the target compound, (S,R)-2-((2-mercaptoacetoxy)methyl)-2_((2-((4-oxo-4-((1RS,2SR)-2,6,6-trimethylcyclohex-3-en-1-yl)butan-2-yl)thio)acetoxy)methyl) propane-1,3-diyl bis(2-((4-oxo-4-((1RS,2SR)-2,6,6-trimethylcyclohex-3-en-1-yl)butan-2-yl)thio)acetate), 2,2-bis((2-((4-oxo-4-((1RS,2SR)-2,6,6-trimethylcyclohex-3-en-1-yl)butan-2-yl)thio)acetoxy)methyl)propane-1,3-diyl bis (2-mercaptoacetate) and 2-((2-mercaptoacetoxy)methyl)-2-((2-((4-oxo-4-((1RS,2SR)-2,6,6-trimethylcyclohex-3-en-1-yl)butan-2-yl)thio)acetoxy)methyl)propane-1,3-diyl bis(2-mercaptoacetate). Removal of traces of volatile impurities under high vacuum at 50° C. gave a mixture (36.3 g) that can be used as such. A pure sample (90%) of the title compound was obtained by flash-chromatography (heptane/MTBE 70:30) on $SiO_2$.

$^{13}$C-NMR: 19.9 (q), 20.7 (q), 21.2/21.4 (q), 29.8 (q), 31.6/31.8 (d), 32.8/32.9 (t), 33.1/33.2 (s), 35.5 (d), 41.7 (t), 42.5 (s), 54.6/54.8 (t), 62.8/62.9 (d), 62.9 (t), 124.1/124.3 (d), 131.7/131.8 (d), 169.9 (s), 211.7/211.8 (s).

$^{1}$H-NMR: 0.87-0.92 (m, 12H); 0.93-1.00 (m, 24H); 1.31-1.33 (m, 12H); 1.66-1.74 (m, 4H); 1.93-2.01 (m, 4H); 2.18-2.24 (m, 4H); 2.47-2.97 (m, 12H); 3.31-3.44 (m, 12H); 4.25 (s, 8H); 5.42-5.48 (m, 4H); 5.51-5.58 (m, 4H).

xviii) Synthesis of (S,R)-2-((2-mercaptoacetoxy) methyl)-2-((2-((4-oxo-4-((1RS,2SR)-2,6,6-trimethylcyclohex-3-en-1-yl)butan-2-yl)thio)acetoxy)methyl) propane-1,3-diylbis(2-((4-oxo-4-((1RS,2SR)-2,6,6-trimethylcyclohex-3-en-1-yl)butan-2-yl)thio)acetate)

Using the same experimental procedure as described in Example xvii, but allowing a shorter reaction time (8 d), yielded a mixture containing the target compound. A pure sample (ca. 80%) was obtained by flash-chromatography (heptane/MTBE 70:30) on $SiO_2$.

$^{13}$C-NMR: 19.9 (q), 20.7 (q), 21.2/21.4 (q), 29.8 (q), 31.6/31.8 (d), 32.8/32.9 (t), 33.1/33.2 (s), 35.4 (d), 41.7 (t), 42.5/42.6 (s), 54.6/54.7 (t), 62.8/62.9 (d), 62.9 (t), 124.1/124.3 (d), 131.7/131.8 (d), 169.9 (s), 211.7/211.8 (s).

$^{1}$H-NMR: 0.87-0.92 (m, 9H); 0.93-1.00 (m, 18H); 1.31-1.33 (m, 9H); 1.66-1.74 (m, 3H); 1.88-2.01 (m, 4H); 2.19-2.25 (m, 3H); 2.47-2.97 (m, 9H); 3.28-3.44 (m, 11H); 4.21-4.25 (m, 8H); 5.42-5.48 (m, 3H); 5.51-5.58 (m, 3H).

xix) Synthesis of 2-methoxyethyl 2-((4-oxo-4-(2,6,6-trimethylcyclohex-3-en-1-yl)butan-2-yl)thio)acetate 2-Methoxyethanol (3.66 g, 48.1 mmol), thioglycolic acid (5.00 ml, 72.2 mmol) and dry toluene (50 ml) were stirred and a catalytic amount of sulfuric acid (one drop) was added. The solution was refluxed overnight. After cooling to room temperature, the solvent was evaporated to give a colorless oil. The oil was taken up in dichloromethane (50 ml) and washed with water (2 twice 20 ml) and brine (40 ml). The organic phase was then dried over sodium sulfate, filtered, and concentrated to give 2-methoxyethyl 2-mercaptoacetate (6.07 g, 84% yield) as a colorless oil.

Delta-damascone (3.00 g, 15.6 mmol), DBU (0.24 ml, 1.6 mmol) and tetrahydrofuran (THF, 20 ml) were heated to 45° C. with stirring. A solution of 2-methoxyethyl 2-mercaptoacetate (15.6 mmol) in THF (10 ml) was added dropwise. The mixture was stirred for 12 h, cooled to room temperature and then concentrated to give a purple oil. The oil was taken up in dichloromethane (50 ml) and successively washed with aqueous HCl (5%, 2×20 ml), water (2×20 ml), and brine (40 ml). The organic phase was dried over sodium sulfate, filtered and concentrated to give a yellow oil with 61% yield.

$^{13}$C-NMR: 19.9 (q), 20.7 (q), 21.1/21.3 (q), 29.8 (q), 31.6/31.8 (d), 32.8/33.0 (t), 33.1/33.2 (s), 35.3 (d), 41.7 (t), 54.7/54.8 (t), 59.0 (q), 62.8/62.9 (d), 64.3 (t), 70.3 (t), 124.1/124.3 (d), 131.7/131.8 (d), 170.6 (s), 211.8/212.0 (s).

$^{1}$H-NMR: 0.86-0.92 (m, 3H); 0.93-1.01 (m, 6H); 1.29-1.36 (m, 3H); 1.65-1.75 (m, 1H); 1.91-2.02 (m, 1H); 2.18-2.25 (m, 1H); 2.45-2.55 (m, 1H); 2.72-2.78 (m, 1H); 2.50-2.60 and 2.92-3.00 (2 m, 1H); 3.27-3.38 (m, 2H); 3.39 (s, 3H); 3.40-3.50 (m, 1H); 3.58-3.65 (m, 2H); 4.26-4.32 (m, 2H); 5.41-5.48 (m, 1H); 5.50-5.58 (m, 1H).

xx) Synthesis of 2,5,8,11-tetraoxatridecan-13-yl 2-((4-oxo-4-(2,6,6-trimethylcyclohex-3-en-1-yl)butan-2-yl)thio)acetate 2,5,8,11-Tetraoxatridecan-13-yl 2-mercaptoacetate was synthesized from 2,5,8,11-tetraoxatridecan-13-ol (3.00 g, 14.4 mmol) and thioglycolic acid (1.50 ml, 21.7 mmol) as described above (Example xix), yielding a colorless oil (88% yield).

This compound (15.6 mmol) in THF (10 ml) was then added to a solution of delta-damascone (3.00 g, 15.6 mmol), DBU (0.24 ml, 1.6 mmol) and THF (20 ml) and treated as described above (Example xix) to give the title compound with 72% yield.

$^{13}$C-NMR: 19.9 (q), 20.7 (q), 21.1/21.3 (q), 29.8 (q), 31.6/31.8 (d), 32.9/33.0 (t), 33.1/33.2 (s), 35.3 (d), 41.7 (t), 54.7/54.8 (t), 59.0 (q), 62.8/62.9 (d), 64.4 (t), 69.0 (t), 70.5/70.6 (t), 71.9 (t), 124.1/124.3 (d), 131.7/131.8 (d), 170.5/170.8 (s), 211.8/211.9 (s).

$^{1}$H-NMR: 0.86-0.92 (m, 3H); 0.93-1.01 (m, 6H); 1.28-1.36 (m, 3H); 1.65-1.75 (m, 1H); 1.91-2.02 (m, 1H); 2.17-2.25 (m, 1H); 2.44-2.57 (m, 1H); 2.72-2.78 (m, 1H); 2.50-2.60 and 2.91-3.00 (2 m, 1H); 3.27-3.37 (m, 2H); 3.38 (s, 3H); 3.40-3.50 (m, 1H); 3.52-3.58 (m, 2H); 3.58-3.69 (m, 10H); 3.69-3.76 (m, 2H); 4.26-4.32 (m, 2H); 5.41-5.48 (m, 1H); 5.50-5.58 (m, 1H).

xxi) Synthesis of 2,5,8,11,14,17,20,23,26,29,32,35-dodecaoxaheptatriacontan-37-yl 2-((4-oxo-4-(2,6,6-trimethylcyclohex-3-en-1-yl)butan-2-yl)thio)acetate (Average Structure)

2,5,8,11,14,17,20,23,26,29,32,35-Dodecaoxaheptatriacontan-37-yl 2-mercaptoacetate (average structure) was synthesized from 2,5,8,11,14,17,20,23,26,29,32,35-dodecaoxaheptatriacontan-37-ol (average structure, $M_n$=500) and thioglycolic acid as described above (Example xix) with 93% yield.

This compound (15.6 mmol) in THF (10 ml) was then added to a solution of delta-damascone (3.00 g, 15.6 mmol), DBU (0.24 ml, 1.6 mmol) and THF (20 ml) and treated as described above (Example xix) to give the title compound with 88% yield.

$^{13}$C-NMR: 19.9 (q), 20.7 (q), 21.1/21.3 (q), 29.8 (q), 31.6/31.8 (d), 31.9 (t), 32.9/33.0 (t), 33.1/33.2 (s), 35.3 (d), 41.7 (t), 54.7/54.8/54.9 (t), 59.0 (q), 62.7/62.8/62.9 (t), 64.4/64.9 (t), 68.9 (t), 70.5/70.6 (t), 71.9 (t), 124.1/124.3 (d), 131.7/131.8 (d), 170.5 (s), 211.8/212.0 (s).

$^1$H-NMR: 0.84-0.92 (m, 3H); 0.93-1.03 (m, 6H); 1.28-1.38 (m, 3H); 1.65-1.75 (m, 1H); 1.91-2.02 (m, 1H); 2.17-2.26 (m, 1H); 2.43-2.57 (m, 1H); 2.72-2.79 (m, 1H); 2.50-2.62 and 2.90-3.01 (2 m, 1H); 3.26-3.37 (m, 2H); 3.38 (s, 3H); 3.39-3.50 (m, 1H); 3.52-3.59 (m, 2H); 3.59-3.69 (m, 40H); 3.69-3.77 (m, 2H); 4.25-4.34 (m, 2H); 5.41-5.48 (m, 1H); 5.50-5.58 (m, 1H).

xxii) Synthesis of (ethane-1,2-diylbis(oxy))bis(ethane-2,1-diyl)bis(2-((4-oxo-4-(2,6,6-trimethylcyclohex-3-en-1-yl)butan-2-yl)thio)acetate)

(Ethane-1,2-diylbis(oxy))bis(ethane-2,1-diyl) bis(2-mercaptoacetate) was synthesized from 2,2'-(ethane-1,2-diylbis(oxy))diethanol (3.61 g, 21.1 mmol) and thioglycolic acid (5.00 ml, 72.2 mmol) as described above (Example xix) to give 6.25 g (87% yield) of a colorless oil.

This compound (2.33 g, 7.8 mmol) in THF (10 ml) was then added to a solution of delta-damascone (3.00 g, 15.6 mmol), DBU (0.24 ml, 1.6 mmol) and THF (20 ml) and treated as described above (Example xix) to give the title compound in 81% yield.

$^{13}$C-NMR: 19.9 (q), 20.7 (q), 21.1/21.3 (q), 29.8 (q), 31.6/31.8 (d), 32.9/33.0 (t), 33.1/33.2 (s), 35.3 (d), 41.7 (t), 54.7/54.8 (t), 62.8/62.9 (d), 64.4 (t), 69.0 (t), 70.6 (t), 124.1/124.3 (d), 131.7/131.8 (d), 170.5 (s), 211.8/211.9 (s).

$^1$H-NMR: 0.85-0.92 (m, 6H); 0.93-1.02 (m, 12H); 1.28-1.36 (m, 6H); 1.65-1.75 (m, 2H); 1.91-2.02 (m, 2H); 2.18-2.25 (m, 2H); 2.44-2.57 (m, 2H); 2.72-2.78 (m, 2H); 2.50-2.60 and 2.91-100 (2 m, 2H); 127-3.39 (m, 4H); 3.39-3.50 (m, 2H); 3.64-3.69 (m, 4H); 3.70-3.75 (m, 4H); 4.26-4.38 (m, 4H); 5.41-5.48 (m, 2H); 5.50-5.58 (m, 2H).

xxiii) Synthesis of methyl 2-((4-oxo-4-((1RS,2SR)-2,6,6-trimethylcyclohex-3-en-1-yl)butan-2-yl)thio)acetate Delta-damascone (10.0 g, 52.0 mmol) and 2-mercaptopropionic acid (5.0 g, 47.1 mmol) were stirred for 48 h at room temperature. The reaction mixture was diluted with MTBE (35 ml), washed several times with $H_2O$ then brine, dried over anhydrous $Na_2SO_4$, filtered and concentrated under vacuum at a maximum temperature of 50° C. The crude title compound (14.0 g), containing some residual delta-damascone, can be used as such. A sample was further purified by flash chromatography on silica gel using a mixture of MTBE and n-heptane (20% up to 40% in MTBE) as the eluent.

$^{13}$C-NMR: 17.2/17.5 (q), 19.9 (q), 20.7 (q), 21.5/21.8 (q), 29.7/29.8 (q), 31.6/31.8 (d), 33.1/33.2 (s), 35.3/35.4 (d), 40.6/41.0 (d), 41.7/41.8 (t), 54.5/55.5 (t), 62.8/62.9 (d), 124.1/124.3 (d), 131.7/131.8 (d), 179.1/179.5 (s), 211.9/212.6 (s).

$^1$H-NMR: 0.87-0.93 (m, 3H); 0.93-1.02 (m, 6H); 1.29-1.37 (m, 3H); 1.42-1.50 (m, 3H); 1.65-1.74 (m, 1H); 1.93-2.01 (m, 1H); 2.18-2.25 (m, 1H); 2.46-2.61 (m, 1.4H); 2.71-2.82 (m, 1H); 2.84-3.08 (m, 0.6H); 3.45-3.63 (m, 2H); 5.42-5.48 (m, 1H); 5.51-5.57 (m, 1H); 10.11 (s, 1H).

xxiv) Synthesis of ammonium 2-((4-oxo-4-((1RS,2SR)-2,6,6-trimethylcyclohex-3-en-1-yl)butan-2-yl)thio)propanoate Delta-damascone (18.2 g, 95 mmol) and ammonium 2-mercaptopropanoate (58% aqueous solution; 16.8 g, 79 mmol) were stirred for 17 h at room temperature. The reaction mixture was diluted with water (20 ml), then extracted with MTBE (3×30 ml). Remaining starting material was recovered from the combined organic phases by removing the solvent under reduced pressure. The aqueous phase containing the target ammonium carboxylate was concentrated under vacuum yielding 21.2 g of the target compound as a white semi-crystalline material (71% yield).

$^{13}$C-NMR: 18.3/18.4 (q), 19.3/19.4 (q), 20.5 (q), 21.0/21.3 (q), 29.1 (q), 30.9/31.2 (d), 32.4/32.5 (s), 33.6/33.7 (d), 40.9/41.0 (t), 42.2/42.5 (d), 54.4/54.5 (t), 61.2/61.4 (d), 124.0/124.2 (d), 131.5/131.6 (d), 174.9/175.0 (s), 212.1 (s).

$^1$H-NMR: 0.81-0.87 (m, 6H); 0.92-0.97 (m, 3H); 1.15-1.21 (m, 3H); 1.22-1.27 (m, 3H); 1.61-1.70 (m, 1H); 1.91-2.01 (m, 1H); 2.24-2.41 (m, 2H); 2.49-2.53 (m, 1H); 2.53-3.02 (m, 2H); 3.27-3.37 (m, 2H); 5.41-5.47 (m, 1H); 5.50-5.56 (m, 1H); 7.40 (broad, $NH_4$).

xxv) Synthesis of 3-((4-oxo-4-((1RS,2SR)-2,6,6-trimethylcyclohex-3-en-1-yl)butan-2-yl)thio)propanoic acid Delta-damascone (41.0 g, 213 mmol) and 3-mercaptopropanoic acid (15.0 g, 141 mmol) were stirred at room temperature for 68 h. The viscous reaction mixture was diluted with MTBE (35 ml), washed several times with $H_2O$ then brine, dried over anhydrous $Na_2SO_4$, filtered and concentrated under vacuum at a maximum temperature of 50° C. The crude title compound (49.0 g), containing some residual delta-damascone, can be used as such. A sample was further purified by flash chromatography on silica gel using a mixture of MTBE and n-heptane (20% up to 50% in MTBE) as the eluent.

$^{13}$C-NMR: 19.9/20.0 (q), 20.7 (q), 21.6/21.8 (q), 25.4/25.6 (t), 29.8 (q), 31.6/31.8 (d), 33.1/33.2 (s), 34.4/34.5 (d), 34.7 (t), 41.7/41.8 (t), 55.0/55.1 (t), 62.9/63.0 (d), 124.1/124.3 (d), 131.8/131.8 (d), 177.9 (s), 212.2/212.3 (s).

$^1$H-NMR: 0.87-0.92 (m, 3H); 0.94-1.00 (m, 6H); 1.29-1.34 (m, 3H); 1.66-1.74 (m, 1H); 1.93-2.01 (m, 1H); 2.18-2.24 (m, 1H); 2.47-2.58 (1.5H); 2.65-2.75 (m, 3H); 2.79-2.85 (m, 2H); 2.88-2.95 (m, 0.5H); 3.28-3.38 (m, 1H); 5.42-5.48 (m, 1H); 5.51-5.57 (m, 1H); 11.25 (s, 1H).

xxvi) Synthesis of trimethylsilyl 3-((4-oxo-4-((1RS,2SR)-2,6,6-trimethylcyclohex-3-en-1-yl)butan-2-yl)thio)propanoate Using the same experimental procedure as described in Example v, the title compound was obtained from the acid described above (Example xxv).

$^{13}$C-NMR: 0.2 (q), 19.9/20.0 (q), 20.8 (q), 21.6/21.8 (q), 25.8/25.9 (t), 29.8 (q), 31.6/31.8 (d), 33.1/33.2 (s), 34.3/34.4 (d), 36.4 (t), 41.8 (t), 55.1/55.2 (t), 62.9/63.0 (d), 124.1/124.2 (d), 131.8/131.9 (d), 172.4 (s), 212.2/212.3 (s).

$^1$H-NMR: 0.29 (s, 9H); 0.87-0.91 (m, 3H); 0.94-1.00 (m, 6H); 1.29-1.33 (m, 3H); 1.65-1.74 (m, 1H); 1.92-2.01 (m, 1H); 2.18-2.24 (m, 1H); 2.46-2.57 (m, 1.5H); 2.58-2.64 (m, 2H); 2.70-2.73 (m, 1H); 2.75-2.81 (m, 2H); 2.87-2.94 (m, 0.5H); 3.27-3.37 (m, 1H); 5.41-5.48 (m, 1H); 5.51-5.57 (m, 1H).

xxvii) Synthesis of methyl 3-((4-oxo-4-((1RS,2SR)-2,6,6-trimethylcyclohex-3-en-1-yl)butan-2-yl)thio)propanoate DBU (2.0 g) was added during 2 min to a mixture of delta-damascone (32.0 g, 166 mmol) and methyl 3-mercaptopropionate (15.0 g, 125 mmol). After 2 h, the reaction was quenched with aqueous citric acid. The reaction mixture was diluted with MTBE (15 ml), washed with $H_2O$ and brine, dried over anhydrous $Na_2SO_4$, filtered and concentrated under high vacuum at a maximum temperature of 50° C. The resulting mixture of the target compound (75%) and delta-damascone (23%) can be used as such. A pure sample (98%; two diastereoisomers ca. 1:1) was obtained by flash-chromatography (heptane/MTBE 95:5) on $SiO_2$.

$^{13}$C-NMR: 19.9 (q), 20.7 (q), 21.6/21.8 (q), 25.7/25.9 (t), 29.8 (q), 31.6/31.8 (d), 33.1/33.2 (s), 34.3 (d), 34.7 (t), 41.7 (t), 51.8 (q), 55.0/55.1 (t), 62.9/63.0 (d), 124.1/124.3 (d), 131.7/131.8 (d), 172.3 (s), 212.1/212.2 (s).

$^{1}$H-NMR: 0.87-0.92 (m, 3H); 0.94-1.01 (m, 6H); 1.29-1.33 (m, 3H); 1.66-1.74 (m, 1H); 1.93-2.01 (m, 1H); 2.18-2.24 (m, 1H); 2.47-2.95 (m, 7H); 3.27-3.37 (m, 1H); 3.70 (s, 3H), 5.42-5.48 (m, 1H); 5.50-5.58 (m, 1H).

xxviii) Synthesis of methyl 3-(((5S)-2-methyl-3-oxo-5-(prop-1-en-2-yl)cyclohexyl)thio)propanoate This compound was prepared from (R)-2-methyl-5-(prop-1-en-2-yl)cyclohex-2-enone (carvone gauche; 28.1 g, 187 mmol), DBU (0.25 g) and methyl 3-mercaptopropionate (27.0 g, 225 mmol) according to the procedure described above (Example xxvii). The resulting crude material (53.2 g), containing some residual carvone can be used as such. Further purification by vacuum distillation (132-140° C., 0.1 mbar) afforded 35.1 g (69% yield) of the pure title compound.

$^{13}$C NMR: 12.6 (q), 20.8 (q), 27.0 (t), 34.6 (t), 35.9 (t), 40.7 (d), 46.0 (t), 48.6 (d), 50.2 (d), 51.8 (q), 110.3 (t), 147.0 (s), 172.1 (s), 209.5 (s).

$^{1}$H-NMR: 1.15 (d, J=6.7, 3H); 1.76 (s, 3H); 1.97-2.07 (m, 1H); 2.15-2.29 (m, 2H); 2.44-2.51 (m, 1H); 2.56-2.63 (m, 2H); 2.74-2.85 (m, 3H); 2.85-2.96 (m, 1H); 3.42-3.48 (m, 1H); 3.70 (s, 3H); 4.71-4.86 (m, 2H).

xxix) Synthesis of methyl 3-((4,4-dimethyl-2-(pent-4-enoyl)cyclohexyl)thio)propanoate (Main Isomer)

This compound was prepared from a mixture of 1-(5,5- and 3,3-dimethylcyclohex-1-enyl)pent-4-en-1-one (Neobutenone®; origin: Firmenich SA; 8.0 g, 41.6 mmol), DBU (0.06 g) and methyl 3-mercaptopropionate (5.0 g, 41.6 mmol) according to the procedure described above (Example xxvii). The resulting crude material (14.0 g), containing the target compound (75%; isomer ratio cis/trans ca. 1:1), 10% of other regioisomers, as well as some residual Neobutenone®, can be used as such. Further purification by vacuum distillation (bulb to bulb distillation, 137-140° C., 0.1 mbar) afforded 8.7 g (67% yield) of title compound (also containing ca. 10% of other regioisomers).

$^{13}$C-NMR (major isomers): 24.2/24.4 (q), 26.4/27.2 (t), 27.3/27.6 (t), 28.0/30.2 (t), 30.0/30.1 (s), 32.4/32.8 (q), 33.1/34.7 (t), 34.9/35.6 (t), 38.9/39.4 (t), 42.5/42.8 (t), 44.6/45.3 (d), 50.2/52.2 (d), 51.7/51.8 (q), 115.0/115.1 (t), 137.3/137.5 (d), 172.3 (s), 210.1/212.0 (s).

$^{1}$H-NMR (major isomers): 0.85-1.02 (m, 6H); 1.06-2.03 (m, 6H); 2.28-2.38 (m, 2H); 2.45-2.82 (m, 8H); 3.67-3.71 (m, 3H); 4.94-5.10 (m, 2H); 5.75-5.90 (m, 1H).

xxx) Synthesis of methyl 3-((7-(pent-4-enoyl)spiro[4.5]decan-8-yl)thio)propanoate-methyl 3-((7-(pent-4-enoyl)spiro[4.5]decan-6-yl)thio)propanoate (mixture)

This compound was prepared from a mixture of 1-(spiro[4.5]dec-7- and 6-en-7-yl)pent-4-en-1-one (Spirogalbanone®; origin: Givaudan SA), DBU and methyl 3-mercaptopropionate according to the procedure described above (Example xxvii).

$^{13}$C-NMR (major isomers): 23.9/24.0 (t), 24.9/25.0 (t), 26.4/27.2 (t), 27.3/27.6 (t), 29.2/30.4 (t), 31.5/31.9 (t), 34.5/34.6 (t), 34.7/34.9 (t), 37.6/39.3 (t), 41.6 (t), 41.9/42.2 (s), 42.1/42.4 (t), 44.6/45.3 (d), 51.6/53.5 (d), 51.7/51.8 (q), 115.0/115.1 (t), 137.3/137.5 (d), 172.3 (s), 210.2/211.9 (s).

$^{1}$H-NMR (major isomers): 1.18-1.81 (m, 14H); 1.82-2.06 (m, 1H); 2.28-2.37 (m, 2H); 2.46-2.69 (m, 5H); 2.70-2.82 (m, 2H); 3.66-3.69 (m, 3H); 4.94-5.08 (m, 2H); 5.76-5.90 (m, 1H).

xxxi) Synthesis of methyl 3-(((1S,1'R,5R)-2,6,6-trimethyl-4'-oxospiro[bicyclo[3.1.1]heptane-3,1'-cyclohexan]-2'-yl)thio)propanoate This compound was prepared from (1S,1'S,2S,5R)-2,6,6-trimethylspiro[bicycle [3.1.1]heptane-3,1'-cyclohex[2]en]-4'-one (Wolfwood®; origin: Firmenich SA), DBU and methyl 3-mercaptopropionate according to the procedure described above (Example xxvii).

$^{13}$C-NMR: 18.8/19.8 (q), 23.6/23.9 (q), 26.3/26.7 (t), 27.0/27.3 (q), 27.1/27.4 (t), 27.4 (q), 34.1/34.6 (t), 36.3 (s), 37.2/37.8 (t), 38.8/39.1 (s), 40.4 (d), 41.4 (t), 41.5/41.6 (d), 43.3/44.0 (t), 46.0 (t), 51.0/51.8 (d), 51.8/54.1 (d), 172.2 (s), 209.0/209.4 (s).

$^{1}$H-NMR: 0.93-1.11 (m, 3H); 1.17-1.27 (m, 4H); 1.28-1.46 (m, 3H); 1.58-1.91 (m, 1H); 1.91-2.18 (m, 5H); 1.92-2.55 (m, 4H); 2.55-2.70 (m, 3H); 2.71-2.90 (m, 2H); 2.91-3.08 (m, 1H); 3.12-3.16 (m, 0.5H); 3.48-3.52 (m, 0.5H); 3.68-3.71 (m, 3H).

xxxii) Synthesis of methyl 3-((3,7-dimethyl-1-oxooct-6-en-3-yl)thio)propanoate

This compound was prepared from (E)-3,7-dimethylocta-2,6-dienal (citral; 10.0 g, 65.7 mmol), DBU (0.1 g) and methyl 3-mercaptopropionate (7.9 g, 65.7 mmol) according to the procedure described above (Example xxvii). The resulting crude material (19.5 g), containing some residual citral can be used as such. Further purification by vacuum distillation (bulb to bulb distillation, 132-140° C., 0.1 mbar) afforded 12.5 g (70% yield) of pure title compound (97%).

$^{13}$C-NMR: 17.7 (q), 22.5 (t), 22.8 (t), 25.7 (q), 26.2 (q), 34.0 (t), 40.8 (t), 46.4 (s), 51.8 (q), 52.4 (t), 123.3 (d), 132.3 (s), 172.1 (s), 201.3 (d).

$^{1}$H-NMR: 1.42 (s, 3H); 1.60-1.70 (m, 8H); 2.03-2.17 (m, 2H); 2.53-2.60 (m, 4H); 2.74-2.80 (m, 2H); 3.70 (s, 3H); 5.05-5.11 (m, 1H); 9.83-9.86 (m, 1H).

xxxiii) Synthesis of methyl 3-((2-formyl-1-phenyloctyl)thio)propanoate

This compound was prepared from (E)-2-benzylideneoctanal (hexylcinnamic aldehyde; origin: Firmenich SA), DBU and methyl 3-mercaptopropionate according to the procedure described above (Example xxvii).

$^{13}$C-NMR: 14.0 (q), 22.4/22.5 (t), 26.0/26.2 (t), 26.5/26.8 (t), 27.4/28.4 (t), 29.0/29.2 (t), 31.4/31.5 (t), 34.2 (t), 49.8/50.5 (d), 51.8 (q), 56.5/56.8 (d), 127.7/127.8 (d); 128.4 (2d), 128.7 (2d), 139.6 (s), 172.1 (s), 202.0/202.6 (d).

$^{1}$H-NMR: 0.77-0.90 (m, 3H); 1.05-1.34 (m, 9H); 1.38-1.78 (m, 1H); 2.37-2.48 (m, 2H); 2.52-2.68 (m, 3H); 3.62-3.66 (m, 3H); 3.94-4.17 (m, 1H); 7.22-7.38 (m, 5H); 9.51-9.62 (m, 1H).

xxxiv) Synthesis of methyl 3-((1-cyano-2,6-dimethyloct-5-en-2-yl)thio)propanoate, (Z/E) Isomeric Mixture This compound was prepared from 3,7-dimethylnona-2,6-dienenitrile (Lemonile®; origin: Givaudan SA), DBU and methyl 3-mercaptopropanoate, according to the procedure described above (Example xxvii).

$^{13}$C-NMR (deduced from the mixture): major (E), 55% of the mixture, 12.7 (q), 16.0 (q), 22.8 (t), 22.9 (t), 25.8 (q), 30.8 (t), 32.3 (t), 34.0 (t), 39.7 (t), 46.3 (s), 51.9 (q), 117.1 (s), 121.3 (d), 138.1 (s), 172.1 (s); minor (Z), 45% of the mixture, 12.8 (q), 16.0 (q), 22.7 (t), 24.8 (t), 25.8 (q), 30.8 (2t), 34.0 (t), 39.9 (t), 46.3 (s), 51.9 (q), 117.1 (s), 122.5 (d), 138.4 (s), 170.9 (s).

$^{1}$H-NMR: 0.95-1.01 (m, 3H); 1.41-1.45 (m, 3H); 1.61-1.63 (m, 2H); 1.64-1.71 (m, 3H); 1.94-2.19 (m, 4H); 2.55-2.61 (m, 2H); 2.64-2.67 (m, 2H); 2.76-2.72 (m, 2H); 3.71 (s, 3H); 5.01-5.12 (m, 1H).

xxxv) Synthesis of methyl 3-((2-cyano-1-phenylethyl)thio)propanoate

This compound was prepared from cinnamonitrile, DBU and methyl 3-mercaptopropionate according to the procedure described above (Example xxvii).

$^{13}$C-NMR: 25.6 (t), 26.6 (t), 34.1 (t), 45.7 (d), 51.9 (q), 117.1 (s), 127.4 (2d), 128.5 (d), 129.1 (2d), 139.0 (s), 171.9 (s).

$^{1}$H-NMR: 2.48-2.53 (m, 2H); 2.65-2.71 (m, 2H); 2.85-2.91 (m, 2H); 3.66 (s, 3H); 4.12-4.19 (m, 1H); 7.28-7.35 (m, 1H); 7.35-7.39 (m, 4H).

xxxvi) Synthesis of methyl 3-((1-cyano-1-phenylpentan-2-yl)thio)propanoate

This compound (ca. 1:1 mixture of diastereoisomers) was prepared from 2-phenylhex-2-enenitrile (Salicynile®; origin: Firmenich SA) and methyl 3-mercaptopropanoate, according to the procedure described above (Example xxvii).

$^{13}$C-NMR: 13.6 (q), 20.1/20.2 (t), 26.9/27.5 (t), 33.5/34.7 (t), 34.8/36.0 (t), 44.6/44.7 (d), 50.8/51.4 (d), 51.8/51.9 (q), 119.1/119.2 (s), 128.2 (d), 128.3 (d), 128.4/128.5 (d), 128.8 (d), 128.9 (d), 133.7/133.8 (s), 172.0/172.1 (s).

$^{1}$H-NMR: 0.82-0.94 (m, 3H); 1.22-1.72 (m, 4H); 2.37-2.59 (m, 3H); 2.65-2.71 (m, 1H); 2.88-2.97 (m, 1H); 3.64-3.71 (m, 3H); 4.08-4.16 (m, 1H); 7.33-7.42 (m, 5H).

xxxvii) Synthesis of methyl 3-((1-(cyano(phenyl)methyl)cyclohexyl)thio)propanoate This compound was prepared from 2-cyclohexylidene-2-phenylacetonitrile (Peonile®; origin: Givaudan SA) and methyl 3-mercaptopropanoate, according to the procedure described above (Example xxvii).

$^{13}$C-NMR: 21.5 (t), 21.6 (t), 22.6 (t), 25.2 (t), 33.0 (t), 33.4 (t), 33.7 (t), 50.8 (d), 51.8 (q), 52.6 (s), 119.7 (s), 128.3 (2d), 128.5 (d), 130.1 (2d), 132.0 (s), 172.1 (s).

$^{1}$H-NMR: 1.04-1.82 (m, 10H); 2.33-2.53 (m, 4H); 3.69 (s, 3H); 3.95 (s, 1H); 7.34-7.43 (m, 5H).

xxxviii) Synthesis of butyl 3-((4-oxo-4-((1RS,2SR)-2,6,6-trimethylcyclohex-3-en-1-yl)butan-2-yl)thio)propanoate This compound was prepared from delta-damascone, DBU and butyl 3-mercaptopropionate according to the procedure described above (Example xxvii).

$^{13}$C-NMR: 13.7 (q), 19.2 (t), 19.9 (q), 20.8 (q), 21.6/21.8 (q), 25.8/25.9 (t), 29.8 (q), 30.6 (t), 31.6/31.8 (d), 33.1/33.2 (s), 34.3 (d), 34.9 (t), 41.7 (t), 51.8 (q), 55.0/55.2 (t), 62.9 (d), 64.8 (t), 124.1/124.3 (d), 131.7/131.8 (d), 172.0 (s), 212.1/212.2 (s).

$^{1}$H-NMR: 0.87-1.01 (m, 12H); 1.29-1.33 (m, 3H); 1.33-1.44 (m, 2H); 1.58-1.66 (m, 2H); 1.66-1.74 (m, 1H); 1.93-2.01 (m, 1H); 2.18-2.24 (m, 1H); 2.47-2.64 (m, 4H); 2.69-2.73 (m, 1H); 2.77-2.84 (m, 2H); 3.27-3.37 (m, 1H); 4.07-4.13 (m, 2H); 5.42-5.48 (m, 1H); 5.50-5.58 (m, 1H).

xxxix) Synthesis of 2-ethylhexyl 3-((4-oxo-4-((1RS,2SR)-2,6,6-trimethylcyclohex-3-en-1-yl)butan-2-yl)thio)propanoate This compound was prepared from delta-damascone, DBU and 2-ethylhexyl 3-mercaptopropanoate according to the procedure described above (Example xxvii).

$^{13}$C-NMR: 11.0 (q), 14.0 (q), 19.9 (q), 20.7 (q), 21.6/21.8 (q), 23.0 (t), 23.8 (t), 25.8/25.9 (t), 28.9 (t), 29.8 (q), 30.4 (t), 31.6/31.8 (d), 33.1/33.2 (s), 34.3 (d), 34.9 (t), 38.7 (d), 41.7 (t), 55.0/55.1 (t), 62.8/62.9 (d), 67.1 (t), 124.1/124.3 (d), 131.8 (d), 172.1 (s), 212.1/212.2 (s).

$^{1}$H-NMR: 0.87-0.92 (m, 9H); 0.94-1.01 (m, 6H); 1.26-1.40 (m, 11H); 1.53-1.61 (m, 2H); 1.65-1.74 (m, 1H); 1.92-2.01 (m, 1H); 2.18-2.24 (m, 1H); 2.46-2.58 (m, 1H); 2.58-2.65 (m, 2H); 2.70-2.74 (m, 1H); 2.78-2.84 (m, 2H); 3.28-3.37 (m, 1H); 3.99-4.05 (m, 2H); 5.41-5.48 (m, 1H); 5.50-5.58 (m, 1H).

xl) Synthesis of octadecyl 3-((4-oxo-4-((1RS,2SR)-2,6,6-trimethylcyclohex-3-en-1-yl)butan-2-yl)thio)propanoate This compound was prepared from delta-damascone, DBU and stearyl mercaptopropionate according to the procedure described above (Example xxvii).

$^{13}$C-NMR: 14.1 (q), 19.9 (q), 20.7 (q), 21.6/21.8 (q), 22.7 (t), 25.8 (t), 28.6 (t), 29.3 (t), 29.4 (t), 29.7 (t), 29.5 (t), 29.6 (t), 29.6/29.7 (8t), 29.8 (q), 31.6/31.8 (d), 31.9 (t), 33.1/33.2 (s), 34.3 (d), 34.9 (t), 41.7 (t), 55.1/55.2 (t), 62.9/63.0 (d), 64.9 (t), 124.1/124.2 (d), 131.7/131.8 (d), 172.0 (s), 212.1/212.2 (s).

$^{1}$H-NMR: 0.87-0.92 (m, 6H); 0.93-1.01 (m, 6H); 1.21-1.37 (m, 33H); 1.57-1.65 (m, 2H); 1.65-1.74 (m, 1H); 1.93-2.01 (m, 1H); 2.18-2.24 (m, 1H); 2.47-2.57 (m, 2H); 2.57-2.64 (m, 2H); 2.69-2.73 (m, 1H); 2.78-2.84 (m, 2H); 3.27-3.37 (m, 1H); 4.05-4.12 (m, 2H); 5.42-5.48 (m, 1H); 5.50-5.58 (m, 1H).

xli) Synthesis of (S,R)-2-ethyl-2-(((3-((4-oxo-4-((1RS,2SR)-2,6,6-trimethylcyclohex-3-en-1-yl)butan-2-yl)thio)propanoyl)oxy)methyl)propane-1,3-diylbis(3-((4-oxo-4-((1RS,2SR)-2,6,6-trimethylcyclohex-3-en-1-yl)butan-2-yl)thio)propanoate)

Delta-damascone (29.0 g, 151 mmol), DBU (1.0 g) and 2-ethyl-2-((3-mercaptopropanoyloxy)methyl)propane-1,3-diyl bis(3-mercaptopropanoate) (10.0 g, 25.1 mmol) were stirred for 16 h at room temperature. The reaction mixture was diluted with MTBE (15 ml), washed with aqueous citric acid, with water and brine, dried over anhydrous $Na_2SO_4$, filtered and then concentrated under high vacuum at a maximum temperature of 50° C. The resulting mixture (33.0 g) containing delta-damascone, the target compound (main ingredient), (S,R)-2-ethyl-2-(((3-mercaptopropanoyl)oxy)

methyl)propane-1,3-diyl bis(3-((4-oxo-4-((1RS,2SR)-2,6,6-trimethylcyclohex-3-en-1-yl)butan-2-yl)thio)propanoate) and 2-ethyl-2-(((3-((4-oxo-4-((1RS,2SR)-2,6,6-trimethylcyclohex-3-en-1-yl)butan-2-yl)thio)propanoyl)oxy)methyl) propane-1,3-diyl bis(3-mercaptopropanoate) can be used as such. A pure sample (90%) of the title compound was obtained by flash-chromatography (heptane/MTBE 70:30) on $SiO_2$.

$^{13}$C-NMR: 7.4 (q), 19.9/20.0 (q), 20.7 (q), 21.6/21.8 (q), 22.9 (t), 25.7/25.9 (t), 29.8 (q), 31.6/31.8 (d), 33.1/33.2 (s), 34.4 (d), 34.8 (t), 40.8 (s), 41.7 (t), 55.0/55.1 (t), 62.8/62.9 (d), 63.9 (t), 124.1/124.3 (d), 131.7/131.8 (d), 171.5 (s), 212.1/212.2 (s).

$^{1}$H-NMR: 0.86-0.92 (m, 12H); 0.93-1.00 (m, 18H); 1.28-1.32 (m, 9H); 1.46-1.53 (m, 2H); 1.65-1.74 (m, 3H); 1.93-2.01 (m, 3H); 2.18-2.24 (m, 3H); 2.46-2.94 (m, 21H); 3.26-3.36 (m, 3H); 4.06 (s, 6H); 5.42-5.48 (m, 3H); 5.50-5.57 (m, 3H).

xlii) Synthesis of (S,R)-2,2-bis(((3-((4-oxo-4-((1RS,2SR)-2,6,6-trimethylcyclohex-3-en-1-yl)butan-2-yl)thio)propanoyl)oxy)methyl)propane-1,3-diyl bis(3-((4-oxo-4-((1RS,2SR)-2,6,6-trimethylcyclohex-3-en-1-yl)butan-2-yl)thio)propanoate)

Delta-damascone (24.0 g, 125 mmol), DBU (0.5 g) and pentaerythritol tetra(3-mercaptopropionate) (10.0 g, 20.5 mmol) were stirred for 4 h at room temperature. The reaction mixture was diluted with MTBE (15 ml), washed with aqueous citric acid, with water (3×10 ml) and brine (10 ml), dried over anhydrous $Na_2SO_4$, filtered and then concentrated under high vacuum at a maximum temperature of 50° C. The resulting mixture (26.9 g) containing delta-damascone, the target compound (main ingredient), (S,R)-2-(((3-mercaptopropanoyl)oxy)methyl)-2-(((3-((4-oxo-4-((1S,2R)-2,6,6-trimethylcyclohex-3-en-1-yl)butan-2-yl)thio)propanoyl) oxy)methyl)propane-1,3-diyl bis(3-((4-oxo-4-((1RS,2SR)-2,6,6-trimethylcyclohex-3-en-1-yl)butan-2-yl)thio) propanoate), 2,2-bis(((3-((4-oxo-4-((1RS,2SR)-2,6,6-trimethylcyclohex-3-en-1-yl)butan-2-yl)thio)propanoyl) oxy)methyl)propane-1,3-diyl bis(3-mercaptopropanoate) and 2-(((3-mercaptopropanoyl)oxy)methyl)-2-(((3-((4-oxo-4-((1RS,2SR)-2,6,6-trimethylcyclohex-3-en-1-yl)butan-2-yl)thio)propanoyl)oxy)methyl)propane-1,3-diyl bis(3-mercaptopropanoate) can be used as such. A sample was further purified by flash chromatography on silica gel using a mixture of MTBE and n-heptane (20% up to 30% in MTBE) as the eluent.

$^{13}$C-NMR: 19.9/20.0 (q), 20.7 (q), 21.6/21.8 (q), 25.7/25.8 (t), 29.8 (q), 31.6/31.8 (d), 33.1/33.2 (s), 34.5 (d), 34.7 (t), 41.7 (t), 42.1 (s), 55.0/55.1 (t), 62.2 (t), 62.8/62.9 (d), 124.1/124.3 (d), 131.7/131.8 (d), 171.5 (s), 212.1/212.2 (s).

$^{1}$H-NMR: 0.86-0.92 (m, 12H); 0.93-1.00 (m, 24H); 1.29-1.33 (m, 12H); 1.65-1.74 (m, 4H); 1.93-2.01 (m, 4H); 2.18-2.24 (m, 4H); 2.46-2.94 (m, 28H); 3.26-3.36 (m, 4H); 4.16 (s, 8H); 5.42-5.48 (m, 4H); 5.50-5.57 (m, 4H).

xliii) Synthesis of N,N-dimethyl-3-((4-oxo-4-((1RS,2SR)-2,6,6-trimethylcyclohex-3-en-1-yl)butan-2-yl)thio)propanamide Delta-damascone (4.39 g, 22.8 mmol), S-3-(dimethylamino)-3-oxopropyl ethanethioate (4.0 g, 22.8 mmol) and DBU (0.17 g, 1.1 mmol) were dissolved in methanol (3.7 ml) and stirred for 4.5 h at room temperature. The reaction mixture was diluted with MTBE (15 ml), washed first with aqueous citric acid, then with water and concentrated under vacuum (at a maximum temperature of 50° C. The crude title compound (8.0 g, ca. 1:1 diastereoisomeric mixture) still contains some residual delta-damascone (12%). It can be used as such. A sample was further purified by flash-distillation (bulb to bulb distillation; 195-200° C., 0.1 mbar).

$^{13}$C-NMR: 19.9/20.0 (q), 20.7 (q), 21.5/21.7 (q), 25.8/25.9 (t), 29.8 (q), 31.6/31.8 (d), 33.1/33.2 (s), 33.6 (t), 34.3 (d), 35.4 (q), 37.1 (q), 41.7 (t), 55.0/55.1 (t), 62.8/62.9 (d), 124.1/124.3 (d), 131.7/131.8 (d), 171.1 (s), 212.3 (s).

$^{1}$H-NMR: 0.87-0.92 (m, 3H); 0.93-1.01 (m, 6H); 1.29-1.34 (m, 3H); 1.65-1.73 (m, 1H); 1.92-2.01 (m, 1H); 2.18-2.25 (m, 1H); 2.46-2.64 (m, 3.5H); 2.70-2.75 (m, 1H); 2.81-2.88 (m, 2H); 2.88-2.93 (m, 0.5H); 0.2.94-2.99 (m, 3H); 2.99-3.05 (m, 3H); 3.28-3.37 (m, 1H); 5.42-5.48 (m, 1H); 5.50-5.58 (m, 1H).

xliv) Synthesis of N,N-dimethyl-3-(((5S)-2-methyl-3-oxo-5-(prop-1-en-2-yl)cyclohexyl)thio)propanamide This compound was prepared from carvone gauche (3.70 g, 22.8 mmol), S-3-(dimethylamino)-3-oxopropyl ethanethioate and DBU in methanol, according to the procedure described above (Example xliii). The crude material, containing some residual carvone, can be used as such. Purification by chromatography ($SiO_2$, heptane/MTBE 80:20 to 20:80) yielded 2.5 g of the pure target compound (97% by GC).

$^{13}$C-NMR: 12.6 (q), 20.3 (q), 25.7 (t), 33.7 (t), 35.5 (q), 37.1 (q), 39.4 (t), 44.3 (d), 46.4 (t), 49.7 (d), 50.6 (d), 110.3 (t), 146.5 (s), 170.9 (s), 209.7 (s).

$^{1}$H-NMR: 1.23 (d, J=6.5, 3H); 1.75 (s, 3H); 1.78-1.91 (m, 1H); 2.29-2.40 (m, 4H); 2.42-2.50 (m, 1H); 2.53-2.63 (m, 3H); 2.87-2.94 (m, 2H); 2.96 (s, 3H); 3.02 (s, 3H); 4.74-4.81 (m, 2H).

xlv) Synthesis of 3-((3,7-dimethyl-1-oxooct-6-en-3-yl)thio)-N,N-dimethylpropanamide This compound was prepared from citral (4.2 g, 27.6 mmol), S-3-(dimethylamino)-3-oxopropyl ethanethioate and DBU in methanol, according to the procedure described above (Example xliii). The crude material, containing some residual citral, can be used as such. Purification by chromatography ($SiO_2$, heptane/MTBE 90:10) yielded 2.0 g of the pure target compound (>99% by NMR, partial decomposition on GC).

$^{13}$C-NMR: 17.7 (q), 22.8 (t), 22.9 (t), 25.6 (q), 26.2 (q), 33.0 (t), 35.4 (q), 37.1 (q), 40.9 (t), 46.4 (s), 52.4 (t), 123.4 (d), 132.2 (s), 170.9 (s), 201.6 (d).

$^{1}$H-NMR: 1.42 (s, 3H); 1.60-1.70 (m, 8H); 2.00-2.24 (m, 2H); 2.50-2.63 (m, 4H); 2.78-2.85 (m, 2H); 2.95 (s, 3H); 2.99 (s, 3H); 5.05-5.11 (m, 1H); 9.83-9.86 (m, 1H).

xlvi) Synthesis of 3-((2-cyano-1-phenylethyl)thio)-N,N-dimethylpropanamide

This compound was prepared from cinnamonitrile (4.0 g, 22.8 mmol), S-3-(dimethylamino)-3-oxopropyl ethanethioate and DBU in methanol, according to the procedure described above (Example xliii). The crude material (6.1 g, containing ca. 30% cinnamonitrile) can be used as such. Purification by flash-distillation (bulb to bulb distillation, 220-225° C., 0.1 mbar) gave 4.1 g of a yellow oil, 95% pure by GC (68% yield).

$^{13}$C-NMR: 25.6 (t), 27.1 (t), 33.4 (t), 35.4 (q), 37.0 (q), 46.0 (d), 117.3 (s), 127.4 (2d), 128.4 (d), 129.0 (2d), 139.5 (s), 170.6 (s).

$^{1}$H-NMR: 2.43-2.50 (m, 2H); 2.72-2.78 (m, 2H); 2.87-2.93 (m, 8H); 4.15-4.20 (m, 1H); 7.27-7.33 (m, 1H); 7.33-7.41 (m, 4H).

xlvii) Synthesis of 2-methyl-3-((4-oxo-4-((1RS,2SR)-2,6,6-trimethylcyclohex-3-en-1-yl)butan-2-yl)thio)propanoic acid Delta-damascone (9.0 g, 46.8 mmol) and 3-mercapto-2-methylpropanoic acid (5.0 g, 41.6 mmol) were stirred for 72 h at room temperature. The reaction mixture was diluted with MTBE (30 ml), washed several times with $H_2O$ and concentrated under vacuum at a maximum temperature of 50° C. The crude title compound (14.5 g), containing some residual delta-damascone, can be used as such. Further purification by flash chromatography on silica gel using a mixture of MTBE and n-heptane (20% up to 40% in MTBE) as the eluent afforded 10.5 g (yield 81%) of 95% pure target compound.

$^{13}$C-NMR: 16.6/16.8 (q), 19.9 (q), 20.7 (q), 21.6/21.9 (q), 29.8 (q), 31.6/31.8 (d), 331/33.2 (s), 33.8/34.0 (t), 34.7/34.9 (d), 40.1/40.3 (d), 41.7 (t), 551/55.2 (t), 62.9/62.9 (d), 124.1/124.3 (d), 131.7/131.8 (d), 181.3/181.5 (s), 212.2/212.4 (s).

$^{1}$H-NMR: 0.86-0.92 (m, 3H); 0.93-1.02 (m, 6H); 1.26-1.34 (m, 6H); 1.65-1.74 (m, 1H); 1.93-2.01 (m, 1H); 2.18-2.25 (m, 1H); 2.46-2.58 (m, 1.4H); 2.58-2.66 (m, 1H); 2.69-2.76 (m, 2H); 2.86-2.94 (m, 1H); 2.94-2.96 (m, 0.6H); 3.25-3.37 (m, 1H); 5.42-5.48 (m, 1H); 5.51-5.57 (m, 1H); 11.05 (s, 1H).

xlviii) Synthesis of 2-((4-oxo-4-((1RS,2SR)-2,6,6-trimethylcyclohex-3-en-1-yl)butan-2-yl)thio)succinic acid Delta-damascone (23.0 g, 120 mmol), mercaptosuccinic acid (6.0 g, 40 mmol) and dimethylsulfoxide (DMSO; 20 ml) were stirred for 93 h at room temperature. The solvent and the excess of delta-damascone were removed by vacuum distillation (bulb to bulb distillation, 90-140° C., 0.1 mbar) to yield the title compound (7.5 g, 55% yield). The resulting 95% pure material can be used as such.

$^{13}$C-NMR: 19.9 (q), 20.7 (q), 21.5/21.9 (q), 29.8 (q), 31.6/31.8 (d), 33.1/33.2 (t), 35.9/36.2 (d), 36.5 (t), 40.8/41.3 (d), 41.7 (t), 54.3/55.2 (t), 62.8/62.9 (d), 124.1/124.3 (d), 131.7/131.8 (d), 176.7/176.8 (s), 177.8/178.1 (s), 211.9/212.5 (s).

$^{1}$H-NMR: 0.85-0.92 (m, 3H); 0.92-1.02 (m, 6H); 1.33-1.39 (m, 3H); 1.66-1.74 (m, 1H); 1.93-2.01 (m, 1H); 2.19-2.25 (m, 1H); 2.46-2.58 (m, 1H); 2.70-3.09 (m, 4H); 3.51-3.63 (m, 1H); 3.67-3.84 (m, 1H); 5.42-5.48 (m, 1H); 5.50-5.58 (m, 1H); 11.47 (s, 2H).

xlix) Synthesis of 4-((4-oxo-4-((1RS,2SR)-2,6,6-trimethylcyclohex-3-en-1-yl)butan-2-yl)thio)butanoic acid Delta-damascone (3.0 g, 15.6 mmol) and 4-mercaptobutanoic acid (2.0 g, 16.6 mmol) were stirred for 5 d at room temperature. Unreacted starting material, as well as dihydrothiophen-2(3H)-one, generated as a by-product, was removed by vacuum distillation (bulb to bulb distillation, 90-140° C., 0.1 mbar) to yield the title compound (0.6 g, ca. 1:1 diastereoisomeric mixture, 12% yield).

$^{13}$C-NMR: 19.9/20.0 (q), 20.8 (q), 21.6/21.8 (q), 24.5 (t), 29.8 (q), 30.0/30.1 (t), 31.6/31.8 (d), 32.8 (t), 33.1/33.2 (s), 34.0/34.1 (d), 41.8 (t), 55.1/55.2 (t), 62.9/63.0 (d), 124.1/124.3 (d), 131.7/131.8 (d), 179.4 (s), 212.4/212.5 (s).

$^{1}$H-NMR: 0.87-0.92 (m, 3H); 0.94-1.00 (m, 6H); 1.27-1.33 (m, 3H); 1.66-1.74 (m, 1H); 1.88-2.08 (m, 3H); 2.18-2.24 (m, 1H); 2.47-2.78 (m, 7H); 3.26-3.36 (m, 1H); 5.42-5.48 (m, 1H); 5.51-5.58 (m, 1H); 11.23 (s, 1H).

l) Synthesis of trimethylsilyl 4-((4-oxo-4-((1RS,2SR)-2,6,6-trimethylcyclohex-3-en-1-yl)butan-2-yl)thio)butanoate Using the experimental procedure described above (Example v) the title compound was obtained from the acid described above (Example xlix).

$^{13}$C-NMR: −0.22 (q), 19.8/19.9 (q), 20.7 (q), 21.6/21.8 (q), 24.9/25.0 (t), 29.8 (q), 30.0/30.1 (t), 31.6/31.8 (d), 33.1/33.2 (s), 34.1 (d), 34.7 (t), 41.8 (t), 55.1/55.2 (t), 62.8/62.9 (d), 124.1/124.2 (d), 131.8/131.9 (d), 173.6 (s), 212.2/212.3 (s).

$^{1}$H-NMR: 0.29 (s, 9H); 0.87-0.92 (m, 3H); 0.94-1.01 (m, 6H); 1.27-1.32 (m, 3H); 1.66-1.74 (m, 1H); 1.84-2.03 (m, 3H); 2.18-2.24 (m, 1H); 2.40-2.62 (m, 6H); 2.68-2.73 (m, 1H); 3.25-3.35 (m, 1H); 5.42-5.48 (m, 1H); 5.51-5.58 (m, 1H).

Example 2

Performance of a Softener Base Comprising an Invention's Compound of Formula (I) as Compared to the Prior-Art The liberation of delta-damascone from the present invention's compounds of formula (I) was tested in a fabric softening surfactant emulsion with the following final composition:

| | |
|---|---|
| Stepantex ® VL90 A (origin: Stepan) | 16.5% by weight |
| Calcium chloride (10% aq. solution) | 0.6% by weight |
| Water | 82.9% by weight |

The different compounds prepared in Example 1 were individually dissolved in ethanol (3 ml) at a concentration to release a total amount of 0.135 mmol of the fragrance and then dispersed in the above described fabric softening surfactant emulsion (5.40 g). The samples were shaken and left standing overnight.

In a beaker, the fabric softening surfactant emulsion containing the compound of formula (1) (2.60 g) was diluted with demineralised cold tap water (600 g) and one cotton sheet (EMPA cotton test cloth Nr. 221, origin: Eidgenössische Materialprüfanstalt (EMPA), pre-washed with an unperfumed detergent powder and cut to ca. 12×12 cm sheets) was added to each beaker. The sheet was manually stirred for 3 min, left standing for 2 min, then wrung out by hand and line-dried for 1 or 3 days. As a reference sample, the prior art compound 3-(dodecylthio)-1-(2,6,6-trimethyl-3-cyclohexen-1-yl)-1-butanone (described as Example 4a in WO 03/049666) was prepared and treated in the same way as described above. All measurements were performed at least twice.

One dry cotton sheet was put into a headspace sampling cell (internal volume ca. 160 ml), thermostated at 25° C. and exposed to a constant air flow (200 ml/min), respectively. The air was filtered through active charcoal and aspirated through a saturated solution of NaCl, corresponding to a constant humidity of ca. 75%. During 15 min, the volatiles were adsorbed onto a waste Tenax® cartridge, then during 15 min onto a clean Tenax® cartridge. The sampling was repeated 7 times every 60 min (45 min trapping on the waste cartridge and 15 min on a clean cartridge); the waste cartridges were discarded. The cartridges with the volatiles were thermally desorbed on a Perkin Elmer TurboMatrix ATD desorber coupled to an Agilent Technologies 7890A GC System equipped with a HP-1 capillary column (30 m, i.d. 0.32 mm, film 0.25 μm) and a flame ionization detector (FID). The volatiles were analyzed using a temperature gradient from 60° C. to 200° C. at 15° C./min. Headspace concentrations (in ng/l of air) were obtained by external standard calibration with different concentrations of the delta-damascone to be liberated. The headspace concentrations measured after 150 min of sampling above the dry cotton sheets are listed in the tables below.

TABLE

Average headspace concentrations of delta-damascone released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666) in a fabric softener application after drying for 1 day and sampling for 150 min.

| Compound from | Amount of α, β-unsaturated ketone, aldehyde or nitrile released [ng/1] | Factor of increase with respect to the prior-art reference |
|---|---|---|
| Prior art (WO 03/049666) | 24.2 | 1.0 |
| Example 1 xlviii | 51.2 | 2.0 |
| Example 1 xxiv | 62.9 | 2.6 |
| Example 1 xxiii | 82.8 | 3.4 |

TABLE

Average headspace concentrations of delta-damascone released from the compounds of formula (I) as prepared in Example 1 and from prior art 3-(dodecylthio)-1-(2,6,6-trimethyl-3-cyclohexen-1-yl)-1-butanone (described as Example 4a in WO 03/049666) in a fabric softener application after drying for 3 days and sampling for 150 min.

| Compound from | Amount of α, β-unsaturated ketone, aldehyde or nitrile released [ng/1] | Factor of increase with respect to the prior-art reference |
|---|---|---|
| Prior art (WO 03/049666) | 113.2 | 1.0 |
| Example 1 xv | 130.6 | 1.7 |
| Example 1 xxxviii | 132.0 | 1.7 |
| Example 1 i | 190.3 | 1.7 |
| Example 1 v | 207.6 | 1.8 |
| Example 1 xxiii | 207.9 | 1.8 |
| Example 1 xlvii | 233.0 | 2.1 |
| Example 1 xxvii | 250.1 | 2.2 |
| Example 1 xlviii | 256.1 | 2.3 |
| Example 1 iv | 277.4 | 2.5 |

The data show that the compounds of formula (I) as prepared in Example 1 release considerably more delta-damascone in a fabric softener application after 1 day and 3 days than the prior art 3-(dodecylthio)-1-(2,6,6-trimethyl-3-cyclohexen-1-yl)-1-butanone (described as Example 4a in WO 03/049666).

Example 3

Performance of a Softener Base Comprising an Invention's Compound of Formula (I) as Compared to the Unmodified α,β-Unsaturated Ketone, Aldehyde or Nitrile to be Released The liberation of an α,β-unsaturated ketone, aldehyde or nitrile from the present invention's compounds of formula (I) was tested in a fabric softening surfactant emulsion as described above in Example 2. As a reference sample, a solution containing an equimolar amount of unmodified α,β-unsaturated ketone, aldehyde or nitrile to be liberated from the compounds of formula (I) was added to a sample of the fabric softening surfactant emulsion and was treated as described above in Example 2. All measurements were performed at least twice. The headspace concentrations measured after 150 min of sampling above the dry cotton sheets are listed in the tables below and compared to the headspace concentrations of the corresponding unmodified α,β-unsaturated ketone, aldehyde or nitrile to be released from the compounds of formula (I) used as the reference.

TABLE

Average headspace concentrations of α, β-unsaturated ketones, aldehydes or nitriles released from the compounds of formula (I) as prepared in Example 1 and of the corresponding unmodified α, β-unsaturated ketone, aldehyde or nitrile in a fabric softener application after drying for 1 day and sampling for 150 min.

| Compound from | Amount of unsaturated ketone, aldehyde or nitrile released [ng/1] | Amount of α, β-unmodified unsaturated ketone, aldehyde or nitrile released [ng/1] | Factor of increase with respect to the prior-art reference |
|---|---|---|---|
| Example 1 ix | 11.9 | 1.7 | 7.0 |
| Example 1 xiii | 25.3 | 1.7 | 14.9 |
| Example 1 iv | 20.4 | 1.7 | 12.0 |
| Example 1 vi | 11.0 | 1.7 | 6.5 |
| Example 1 xxvii | 20.2 | 1.7 | 11.9 |
| Example 1 xliii | 12.8 | 1.7 | 7.5 |
| Example 1 xix | 8.1 | 1.7 | 4.8 |
| Example 1 xx | 6.3 | 1.7 | 3.7 |
| Example 1 xxi | 13.4 | 1.7 | 7.9 |
| Example 1 xxii | 22.3 | 1.7 | 13.1 |
| Example 1 vii | 9.3 | 1.4 | 6.6 |
| Example 1 xxxvi | 3.4 | 1.0 | 3.4 |
| Example 1 xxix | 1.7 | 0.3 | 5.7 |
| Example 1 xxviii | 28.0 | 0.1* | 280.0 |
| Example 1 ii | 40.4 | 9.3 | 4.3 |
| Example 1 xxxiii | 15.7 | 11.1 | 1.4 |
| Example 1 iii | 15.1 | 11.1 | 1.4 |
| Example 1 xxxii | 35.7 | 0.1* | 357.0 |

*no compound was detected and a value of 0.1 ng/l was taken as the minimum of detection.

TABLE

Average headspace concentrations of α, β-unsaturated ketones, aldehydes or nitriles released from the compounds of formula (I) as prepared in Example 1 and of the corresponding unmodified α, β-unsaturated ketone, aldehyde or nitrile in a fabric softener application after drying for 3 days and sampling for 150 mm.

| Compound from | Amount of α, β-unsaturated ketone, aldehyde or nitrile released [ng/1] | Amount of α, β-unmodified unsaturated ketone, aldehyde or nitrile released [ng/1] | Factor of increase with respect to the prior-art reference |
|---|---|---|---|
| Example 1 xi | 10.6 | 1.2 | 8.8 |
| Example 1 xvi | 44.4 | 1.2 | 37.0 |

TABLE-continued

Average headspace concentrations of α, β-unsaturated ketones, aldehydes or nitriles released from the compounds of formula (I) as prepared in Example 1 and of the corresponding unmodified α, β-unsaturated ketone, aldehyde or nitrile in a fabric softener application after drying for 3 days and sampling for 150 mm.

| Compound from | Amount of α, β-unsaturated ketone, aldehyde or nitrile released [ng/l] | Amount of α, β-unmodified unsaturated ketone, aldehyde or nitrile released [ng/l] | Factor of increase with respect to the prior-art reference |
|---|---|---|---|
| Example 1 xvii | 33.5 | 1.2 | 27.9 |
| Example 1 vi | 83.8 | 1.2 | 69.8 |
| Example 1 x | 27.4 | 1.2 | 22.8 |
| Example 1 xxxix | 20.2 | 1.2 | 16.8 |
| Example 1 xxv | 80.5 | 1.2 | 67.1 |
| Example 1 xxvi | 104.5 | 1.2 | 87.1 |
| Example 1 xli | 54.4 | 1.2 | 45.3 |
| Example 1 xlii | 17.7 | 1.2 | 14.8 |
| Example 1 xlix | 48.6 | 1.2 | 40.5 |
| Example 1 xxi | 63.2 | 1.2 | 52.7 |
| Example 1 xl | 93.4 | 1.2 | 77.8 |
| Example 1 xiv | 73.7 | 1.2 | 61.4 |

The data show that the compounds of formula (I) as prepared in Example 1 release considerably more α,β-unsaturated ketone, aldehyde or nitrile in a fabric softener application after 1 day and 3 days than the unmodified α,β-unsaturated ketone, aldehyde or nitrile reference sample.

Example 4

Performance of an All Purpose Cleaner Comprising an Invention's Compound of Formula (I)

The use as perfuming ingredient of the present invention's compounds of formula (I) has been tested in an all purpose surface cleaner (APC). An APC base with the following final composition has been prepared:

| | |
|---|---|
| Neodol ® 91-8 (origin: Shell Chemicals) | 5.0% by weight |
| Marlon ® A 375 (origin: Hüls AG) | 4.0% by weight |
| Sodium cumolsulphonate | 2.0% by weight |
| Kathon ® CG (origin: Rohm and Haas) | 0.2% by weight |
| Water | 88.8% by weight |

One of the invention's compounds of formula (I) was weighed into the APC base (1 ml) at a concentration to release a total amount of 0.012 mmol of the fragrance. Then the sample was diluted with demineralized tap water (9 ml). Another sample containing the unmodified α,β-unsaturated ketone, aldehyde or nitrile to be released (0.3 mmol) instead of the invention's compound of formula (I) was prepared in the same way as the reference. The samples were shaken and then deposited as a film onto a porous ceramic plate (ca. 5×10 cm) by carefully pipetting 0.75 ml of the diluted samples onto the surface of the substrate. The samples were then covered with a ca. 2.5 1 crystallizing dish and left standing at room temperature. After one day, the substrates were placed inside a headspace sampling cell (ca. 625 ml) and exposed to a constant air flow of ca. 200 ml/min. The air was filtered through active charcoal and aspirated through a saturated solution of NaCl (to ensure a constant humidity of the air of ca. 75%). During 135 min the headspace system was left equilibrating, and then the volatiles were adsorbed during 15 minutes on a clean Tenax® cartridge. The cartridges were desorbed and analyzed as described in Example 2. All measurements were performed at least twice.

The headspace concentrations measured after 150 min of sampling above the porous ceramic plate are listed in the table below and compared to the headspace concentrations of the corresponding unmodified α,β-unsaturated ketone, aldehyde or nitrile to be released from the compounds of formula (I) used as the reference.

TABLE

Average headspace concentrations of α, β-unsaturated ketones, aldehydes or nitriles released from the compounds of formula (I) as prepared in Example 1 and of the corresponding unmodified α, β-unsaturated ketone, aldehyde or nitrile in an all purpose cleaner application after 1 day and sampling for 150 min.

| Compound from | Amount of α, β-unsaturated ketone, aldehyde or nitrile released [ng/l] | Amount of α, β-unmodified unsaturated ketone, aldehyde or nitrile released [ng/l] | Factor of increase with respect to the prior-art reference |
|---|---|---|---|
| Prior art (WO 03/049666) | 16.0 | 13.7 | 1.2 |
| Example 1 xxv | 21.6 | 13.7 | 1.6 |
| Example 1 xxvii | 26.1 | 13.7 | 1.9 |
| Example 1 xxiii | 53.9 | 13.7 | 3.9 |
| Example 1 xxi | 39.4 | 13.7 | 2.8 |

The data show that the compounds of formula (I) as prepared in Example 1 release considerably more α,β-unsaturated ketone, aldehyde or nitrile in a fabric softener application after 1 day and 3 days than the unmodified α,β-unsaturated ketone, aldehyde or nitrile or the prior art 3-(dodecylthio)-1-(2,6,6-trimethyl-3-cyclohexen-1-yl)-1-butanone (described as Example 4a in WO 03/049666).

The invention claimed is:

1. A method to confer, enhance, improve or modify the odor properties of a perfuming composition or of a perfumed article, which method comprises adding to said composition or article an effective amount of at least a compound of formula (I):

(I)

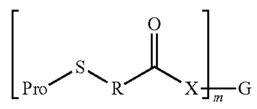

wherein:

a) m represents an integer from 1 to 2;

b) Pro represents a hydrogen atom or a group susceptible of generating an odoriferous α,β-unsaturated ketone, aldehyde or nitrile that is represented by the formulae (P-1)

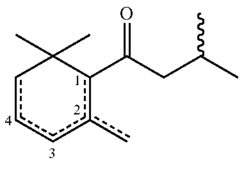

-continued (P-2)

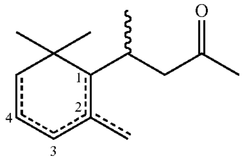

(P-3)

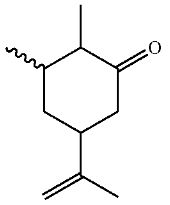

(P-4)

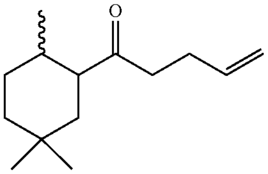

(P-5)

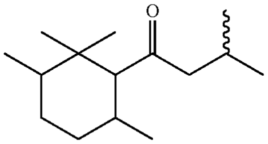

(P-6)

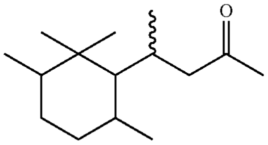

(P-7)

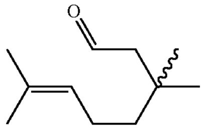

(P-8)

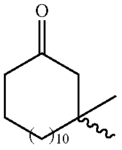

(P-9)

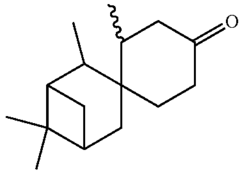

(P-10)

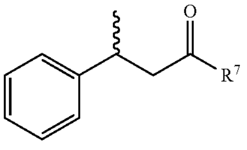

-continued (P-11)

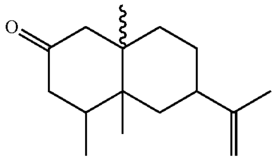

(P-12)

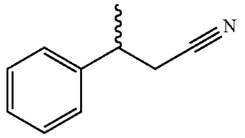

(P-13)

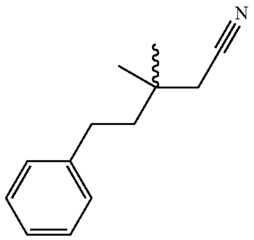

(P-14)

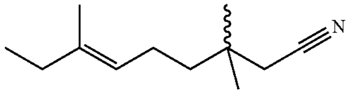

(P-15)

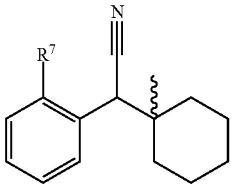

(P-16)

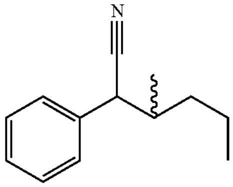

in which formulae the wavy line indicates the location of the bond between said Pro and the S atom, the dotted lines represent a single or double bond, $R^7$ indicating a hydrogen atom or a methyl group;

and with the proviso that at least one of the Pro groups is of the formulae (P-1) to (P-16) as defined hereinabove;

c) X represents an oxygen atom;

d) R represents a linear or branched $C_1$-$C_3$, alkanediyl group optionally comprising a carboxylic acid or an alkaline carboxylate group; and e) G represents a hydrogen atom, an ammonium cation or a $C_{1-8}$ quaternary amine cation or a methyl or ethyl group.

2. The method according to claim 1, characterized in that said group Pro is a group of the formulae (P-1) to (P-11).

3. The method according to claim 1, characterized in that said group Pro is a group of the formulae (P-1) to (P-7).

4. The method according to claim 1, characterized in that said group Pro is a group susceptible of generating an odoriferous compound selected from the group consisting of damascones, ionones, beta-damascenone, 1-(5,5- or 3,3- dimethyl-1-cyclohexen-1-yl)-4-penten-1-one, carvone, 1-(2, 2,3,6-tetramethyl-1-cyclohexyl)-2-buten-1-one, 4-(2,2,3,6-tetramethyl-1-cyclohexyl)-3-buten-2-one, and citral.

5. The method according to claim 1, characterized in that said m is 1.

6. The method according to claim 1, characterized in that said group R is a CH(Me), $CH_2$, $CH_2CH_2$, $CH_2CH_2CH_2$, $CH(Me)CH_2$ or a $CH(CH_2COOH)$ or $CH(CH_2COOM)$ group, M being an alkaline metal cation.

7. The method according to claim 1, characterized in that said compound comprises a compound of formula (I')

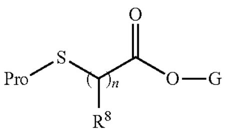

wherein Pro and G have the meaning indicated in claim 1, n is 1 or 2, and $R^8$ represents a hydrogen atom or a methyl group or a $CH_2COOH$ or a $CH_2COOM$ group, with M being an alkaline metal cation or an ammonium cation.

8. A compound of formula (I), (I)

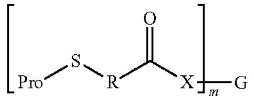

wherein:

a) m represents an integer from 1 to 2;

b) Pro represents a hydrogen atom or a group susceptible of generating an odoriferous α,β-unsaturated ketone, aldehyde or nitrile that is represented by the formulae (P-1)

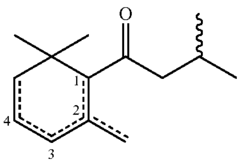

(P-2)

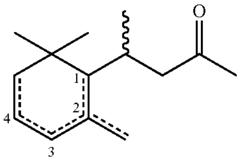

(P-3)

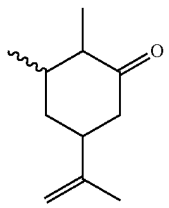

-continued (P-4)

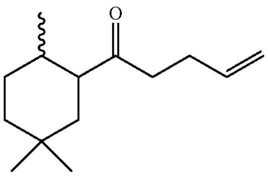

(P-5)

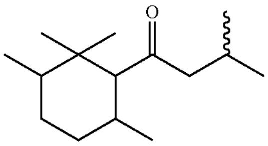

(P-6)

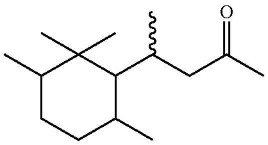

(P-7)

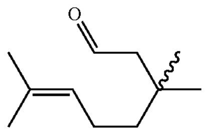

(P-8)

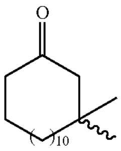

(P-9)

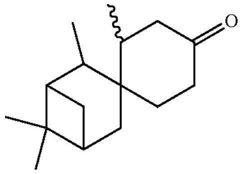

(P-10)

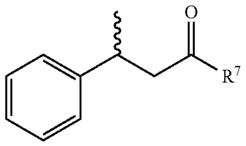

(P-11)

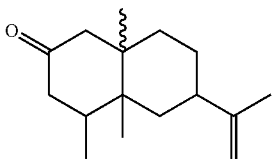

(P-12)

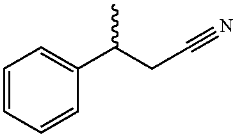

-continued (P-13)

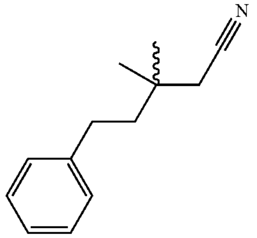

(P-14)

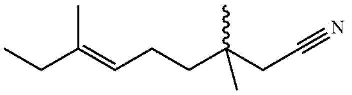

(P-15)

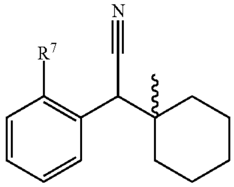

(P-16)

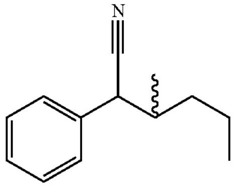

in which formulae the wavy line indicates the location of the bond between said Pro and the S atom, the dotted lines represent a single or double bond, $R^7$ indicating a hydrogen atom or a methyl group;

and with the proviso that at least one of the Pro groups is of the formulae (P-1) to (P-16) as defined hereinabove;

c) X represents an oxygen atom;

d) R represents a linear or branched $C_1$-$C_3$, alkanediyl group optionally comprising a carboxylic acid or an alkaline carboxylate group; and e) G represents a hydrogen atom, an ammonium cation or a $C_{1-8}$ quaternary amine cation or a methyl or ethyl group;

provided that phenylmethyl 2-[[1-methyl-1-(4-methyl-2-oxocyclohexyl)ethyl]thio]-acetate, methyl 2-[[[(1S,2R,5R)-6,6-dimethyl-3-oxobicyclo[3.1.1]hept-2-yl]methyl]thio]-acetate, methyl 2-[(3-oxo-1-phenylbutyl)thio]-acetate, 2-((2-methyl-3-oxo-5-(prop-1-en-2-yl)cyclohexyl)thio)acetic acid, methyl 2-((2-cyano-1-phenylethyl)thio)acetate and ethyl 2-((2-methyl-3-oxo-5-(prop-1-en-2-yl)cyclohexyl)thio)acetate are excluded.

9. A perfuming composition comprising i) as perfuming ingredient, at least one compound of formula (I) as defined in claim 1;

ii) at least one ingredient selected from the group consisting of a perfumery carrier and a perfumery base; and iii) optionally at least one perfumery adjuvant.

10. A perfuming consumer product which comprises i) as perfuming ingredient, at least one compound of formula (I) as defined in claim 1; and ii) a perfumery consumer base.

11. A perfuming consumer product according to claim 10, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a “ready to use” powdered air freshener, a wipe, a dish detergent or hard-surface detergent.

12. A perfuming composition comprising iv) as perfuming ingredient, at least one compound of formula (I) according to claim 8;

v) at least one ingredient selected from the group consisting of a perfumery carrier and a perfumery base; and vi) optionally at least one perfumery adjuvant.

13. A perfuming consumer product which comprises i) as perfuming ingredient, at least one compound of formula (I) according to claim 8; and ii) a perfumery consumer base.

14. A perfuming consumer product according to claim 13, characterized in that the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a “ready to use” powdered air freshener, a wipe, a dish detergent or hard-surface detergent.

15. The method according to claim 1, wherein at least one of the Pro groups is of the formulae (P-12) to (P-16).

16. The compound according to claim 8, wherein at least one of the Pro groups is of the formulae (P-12) to (P-16).

* * * * *